United States Patent
Zucchelli et al.

(10) Patent No.: US 7,152,616 B2
(45) Date of Patent: Dec. 26, 2006

(54) DEVICES AND METHODS FOR PROGRAMMABLE MICROSCALE MANIPULATION OF FLUIDS

(75) Inventors: Piero Zucchelli, Versonnex (FR); Bart Van de Vyver, Geneva (CH)

(73) Assignee: SpinX, Inc. (CH)

( * ) Notice: Subject to any disclaimer, the term of this patent is extended or adjusted under 35 U.S.C. 154(b) by 81 days.

(21) Appl. No.: 10/491,299

(22) PCT Filed: Dec. 4, 2003

(86) PCT No.: PCT/US03/38629

§ 371 (c)(1),
(2), (4) Date: Mar. 30, 2004

(87) PCT Pub. No.: WO2004/050242

PCT Pub. Date: Jun. 17, 2004

(65) Prior Publication Data

US 2005/0109396 A1 May 26, 2005

Related U.S. Application Data

(60) Provisional application No. 60/430,792, filed on Dec. 4, 2002.

(51) Int. Cl.
*F16K 31/02* (2006.01)
*G01N 35/00* (2006.01)
*B01L 3/00* (2006.01)

(52) U.S. Cl. .............. 137/68.11; 422/103; 436/180

(58) Field of Classification Search ............... 137/67, 137/68.11, 72, 74; 422/64, 103; 436/45, 436/180
See application file for complete search history.

(56) References Cited

U.S. PATENT DOCUMENTS 3,736,432 A   5/1973   Sweet (Continued)

FOREIGN PATENT DOCUMENTS

EP   0 392 475 A2   10/1990

(Continued)

*Primary Examiner*—Ramesh Krishnamurthy
(74) *Attorney, Agent, or Firm*—Brown Rudnick Berlack Israels LLP; John C. Serio

(57) ABSTRACT

The present invention is directed generally to devices and methods for controlling fluid flow in meso-scale fluidic components in a programmable manner. Specifically, the present invention is directed to an apparatus and method for placing two microfluidic components in fluid communication at an arbitrary position and time, both of which are externally defined. The inventive apparatus uses electromagnetic radiation to perforate a material layer having selected adsorptive properties. The perforation of the material layer allows the fluid communication between microfluidic components. Other aspects of this invention include an apparatus and method to perform volumetric quantitation of fluids, an apparatus to program arbitrary connections between a set of input capillaries and a set of output capillaries, and a method to transport fluid in centripetal device from a larger to a smaller radius. In addition, the present invention also is directed to a method to determine the radial and polar position of a pickup in the reference frame of a rotating device.

37 Claims, 25 Drawing Sheets

U.S. PATENT DOCUMENTS

| | | |
|---|---|---|
| 4,248,346 A | 2/1981 | Johnson |
| 4,276,048 A | 6/1981 | Leaback |
| 5,125,524 A | 6/1992 | Hosoda et al. |
| 5,160,702 A | 11/1992 | Kopf-Sill et al. |
| 5,180,480 A | 1/1993 | Manz |
| 5,250,263 A | 10/1993 | Manz |
| 5,278,048 A | 1/1994 | Parce et al. |
| 5,304,487 A | 4/1994 | Wilding et al. |
| 5,441,951 A | 8/1995 | Serhan |
| 5,486,335 A | 1/1996 | Wilding et al. |
| 5,547,472 A | 8/1996 | Onishi et al. |
| 5,580,523 A | 12/1996 | Bard |
| 5,585,069 A | 12/1996 | Zanzucchi et al. |
| 5,593,838 A | 1/1997 | Zanzucchi et al. |
| 5,637,469 A | 6/1997 | Wilding et al. |
| 5,789,251 A | 8/1998 | Astle |
| 5,842,787 A | 12/1998 | Kopf-Sill et al. |
| 5,846,396 A | 12/1998 | Zanzucchi et al. |
| 5,858,188 A | 1/1999 | Soane et al. |
| 5,869,002 A | 2/1999 | Limon et al. |
| 5,882,465 A | 3/1999 | McReynolds |
| 5,882,903 A | 3/1999 | Andrevski et al. |
| 5,885,470 A | 3/1999 | Parce et al. |
| 5,892,577 A | 4/1999 | Gordon |
| 5,942,443 A | 8/1999 | Parce et al. |
| 5,972,187 A | 10/1999 | Parce et al. |
| 6,011,252 A | 1/2000 | Jensen |
| 6,030,581 A | 2/2000 | Virtanen |
| 6,039,804 A | 3/2000 | Kim et al. |
| 6,046,056 A | 4/2000 | Parce et al. |
| 6,048,734 A * | 4/2000 | Burns et al. ............... 436/180 |
| 6,063,589 A | 5/2000 | Kellogg et al. |
| 6,080,253 A | 6/2000 | Hitch |
| 6,086,740 A | 7/2000 | Kennedy |
| 6,086,825 A | 7/2000 | Sundberg et al. |
| 6,090,251 A | 7/2000 | Sundberg et al. |
| 6,102,933 A | 8/2000 | Lee et al. |
| 6,123,798 A | 9/2000 | Gandhi et al. |
| 6,143,248 A | 11/2000 | Kellogg et al. |
| 6,149,787 A | 11/2000 | Chow et al. |
| 6,150,180 A | 11/2000 | Parce et al. |
| 6,153,073 A | 11/2000 | Dubrow et al. |
| 6,167,910 B1 | 1/2001 | Chow |
| 6,182,733 B1 | 2/2001 | McReynolds |
| 6,186,660 B1 | 2/2001 | Kopf-Sill et al. |
| 6,213,151 B1 | 4/2001 | Jacobson et al. |
| 6,235,175 B1 | 5/2001 | Dubrow et al. |
| 6,238,538 B1 | 5/2001 | Parce et al. |
| 6,251,343 B1 | 6/2001 | Dubrow et al. |
| 6,256,088 B1 | 7/2001 | Gordon |
| 6,267,858 B1 | 7/2001 | Parce et al. |
| 6,274,089 B1 | 8/2001 | Chow et al. |
| 6,274,337 B1 | 8/2001 | Parce et al. |
| 6,287,517 B1 | 9/2001 | Ackley et al. |
| 6,294,063 B1 | 9/2001 | Becker et al. |
| 6,296,673 B1 | 10/2001 | Santarsiero et al. |
| 6,296,810 B1 | 10/2001 | Ulmer |
| 6,301,931 B1 | 10/2001 | Swierkowski et al. |
| 6,302,134 B1 | 10/2001 | Kellogg et al. |
| 6,306,590 B1 | 10/2001 | Mehta et al. |
| 6,306,659 B1 | 10/2001 | Parce et al. |
| 6,309,601 B1 | 10/2001 | Juncosa et al. |
| 6,316,201 B1 | 11/2001 | Nikiforov |
| 6,316,781 B1 | 11/2001 | Nagle et al. |
| 6,319,468 B1 | 11/2001 | Sheppard, Jr. et al. |
| 6,319,469 B1 | 11/2001 | Mian et al. |
| 6,321,791 B1 | 11/2001 | Chow |
| 6,322,683 B1 | 11/2001 | Wolk et al. |
| 6,327,031 B1 | 12/2001 | Gordon |
| 6,331,439 B1 | 12/2001 | Cherukuri et al. |
| 6,334,301 B1 | 1/2002 | Otsap et al. |
| 6,339,473 B1 | 1/2002 | Gordon |
| 6,340,589 B1 | 1/2002 | Turner et al. |
| 6,342,142 B1 | 1/2002 | Ramsey |
| 6,357,305 B1 | 3/2002 | Witt et al. |
| 6,368,402 B1 | 4/2002 | DeTitta et al. |
| 6,379,974 B1 | 4/2002 | Parce et al. |
| 6,399,023 B1 | 6/2002 | Chow |
| 6,399,361 B1 | 6/2002 | Brotherston et al. |
| 6,399,389 B1 | 6/2002 | Parce et al. |
| 6,409,832 B1 | 6/2002 | Weigl et al. |
| 6,413,782 B1 | 7/2002 | Parce et al. |
| 6,429,025 B1 | 8/2002 | Parce et al. |
| D463,031 S | 9/2002 | Slomski et al. |
| 6,521,451 B1 | 2/2003 | Potter |
| 6,527,432 B1 | 3/2003 | Kellogg et al. |
| 6,620,625 B1 | 9/2003 | Wolk et al. |
| 6,709,869 B1 | 3/2004 | Mian et al. |
| 6,719,862 B1 | 4/2004 | Quick et al. |
| 6,752,966 B1 | 6/2004 | Chazan |
| 6,756,019 B1 | 6/2004 | Dubrow et al. |
| 6,779,559 B1 | 8/2004 | Parce et al. |
| 6,811,736 B1 | 11/2004 | Ohman et al. |
| 6,827,906 B1 | 12/2004 | Bjornson et al. |
| 6,829,753 B1 | 12/2004 | Lee et al. |
| 6,852,851 B1 | 2/2005 | Tooke et al. |
| 6,857,449 B1 | 2/2005 | Chow |
| 6,884,395 B1 | 4/2005 | Tooke et al. |
| 6,885,982 B1 | 4/2005 | Harris et al. |
| 2001/0001060 A1 | 5/2001 | Kellogg et al. |
| 2001/0052976 A1 | 12/2001 | Juncosa et al. |
| 2001/0054702 A1 | 12/2001 | Williams |
| 2002/0027133 A1 | 3/2002 | Kellogg et al. |
| 2002/0033193 A1 | 3/2002 | McNeely et al. |
| 2002/0050456 A1 | 5/2002 | Sheppard, Jr. et al. |
| 2002/0058329 A1 | 5/2002 | Singh et al. |
| 2005/0089449 A1 | 4/2005 | Polwart et al. |

FOREIGN PATENT DOCUMENTS

| | | |
|---|---|---|
| EP | 0 417 305 A1 | 3/1991 |
| EP | 0 553 539 A1 | 8/1993 |
| GB | 2 249 492 A | 5/1992 |
| WO | WO 96/15450 | 5/1996 |
| WO | WO 96/15576 | 5/1996 |
| WO | WO 99/58245 | 11/1999 |
| WO | WO 01/68257 | 9/2001 |
| WO | WO 01/87485 | 11/2001 |
| WO | WO 02/055197 | 7/2002 |
| WO | WO 02/083852 | 10/2002 |
| WO | WO 03/035538 | 5/2003 |

* cited by examiner

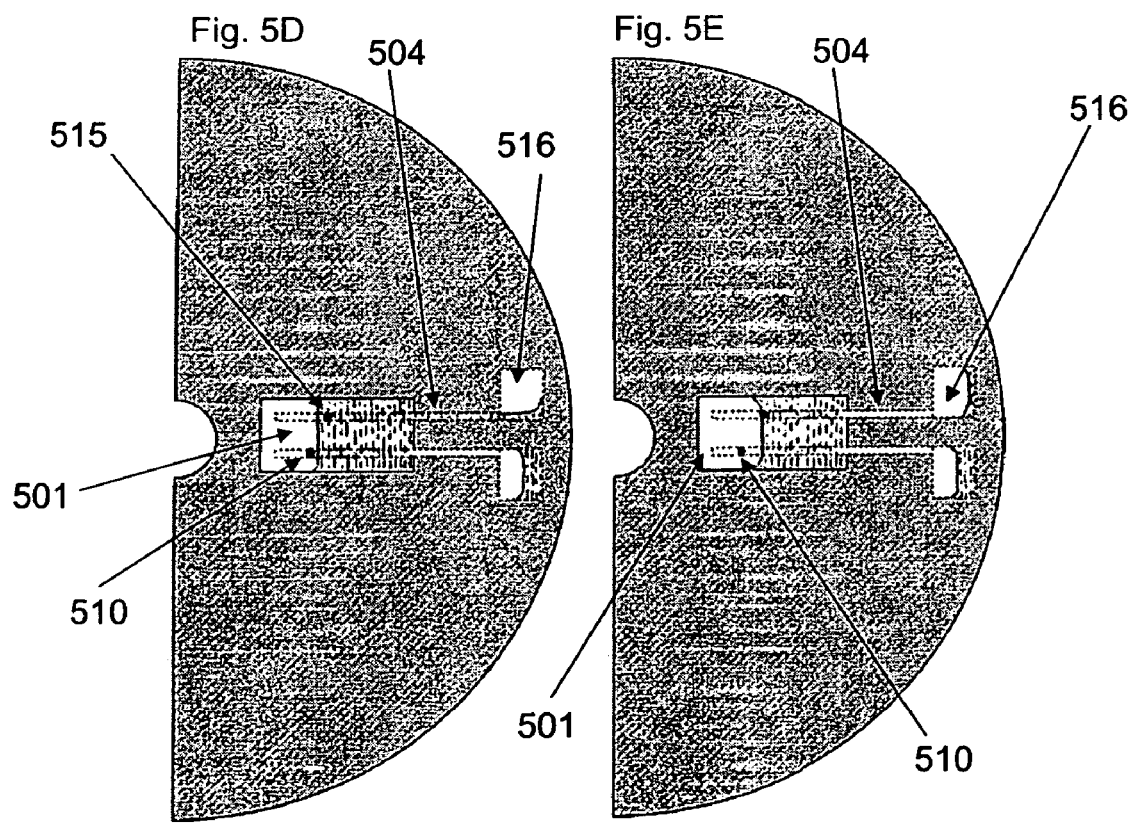

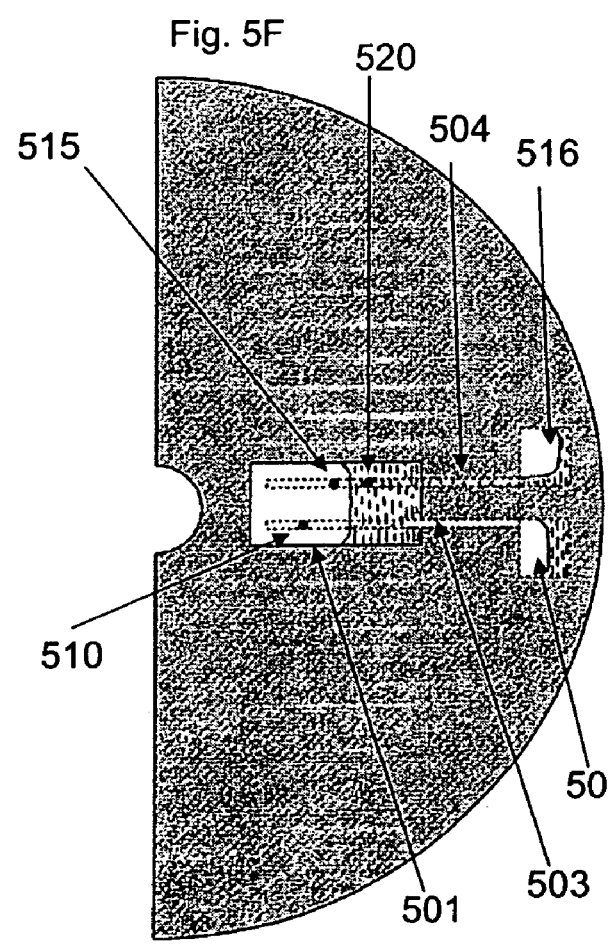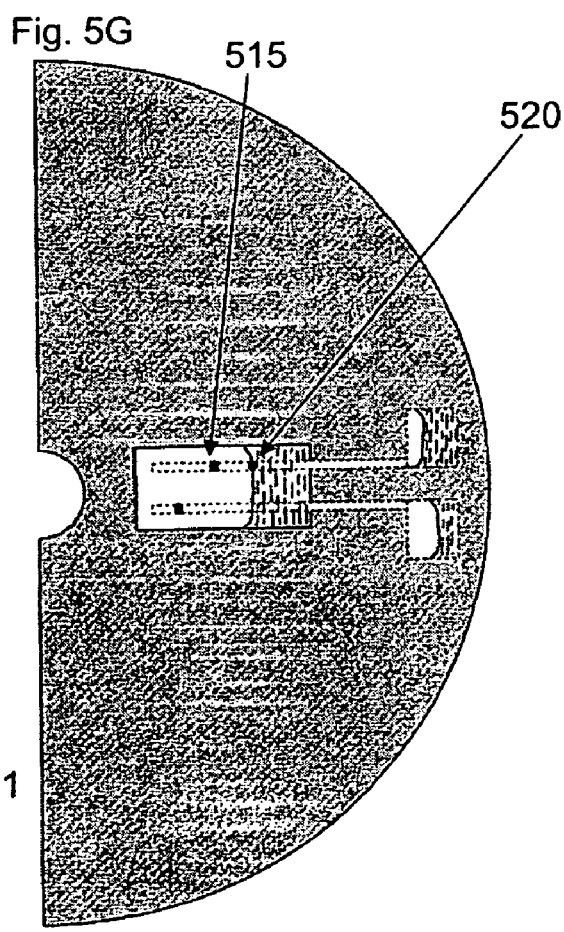

# DEVICES AND METHODS FOR PROGRAMMABLE MICROSCALE MANIPULATION OF FLUIDS

CROSS REFERENCE TO RELATED APPLICATIONS

This application claims the priority of U.S. Provisional Application No. 60/430,792 filed Dec. 4, 2002 entitled "DEVICES AND METHODS FOR PROGRAMMABLE MICROSCALE MANIPULATION OF FLUIDS" the whole of which is herby incorporated by reference herein.

FIELD OF THE INVENTION

The present invention relates to the field of microfluidic circuits for chemical, biological, and biochemical processes or reactions. More specifically, it discloses devices and methods for regulating fluid flow in microstructures in a programmable manner.

BACKGROUND OF THE INVENTION

In recent years, the pharmaceutical, biotechnology, chemical and related industries have increasingly adopted micro-chamber and channel structures for performing various reactions and analyses. The benefits of these structures include miniaturization, reduction in space and cost of reagents and enable one to perform a large number of reactions without human intervention, either in parallel or in series (i.e., one after the other).

Microfluidic devices are by far the most promising candidates to realize a micro-TAS (Micro Total Analysis System). In general, all attempts in this direction can be characterized in two ways: according to the forces responsible for the fluid transport and according to the mechanism used to direct the flow of fluids. The former are referred to as motors. The latter are referred to as valves, and constitute logic or analogue actuators, essential for a number of basic operations such as volumetric quantitation of fluids, mixing of fluids, connecting a set of fluid inputs to a set of fluid outputs, sealing containers (to gas or to liquids passage according to the application) in a sufficiently tight manner to allow fluid storage, regulating the fluid flow speed.

As motors, the prior art disclose a variety of solutions, including electro-kinetic and electro-osmotic transport, mechanical micro-pumps, external pressure, acoustic energy, and the centripetal force. The present invention is concerned primarily, but not exclusively, with the category of centripetal devices. Accordingly, a summary of some of the prior art related to centripetal devices includes: Yamaji et al. (EP00392475A2) and Takase et al. (EP00417305A1) disclose a liquid sample analyser based on a rotating disk; Kellogg et al. (U.S. Pat. No. 6,063,589/WO0187485A2) and Mian et al. (U.S. Pat. No. 6,319,469, US21055812A1) disclose devices and methods for using centripetal acceleration to drive fluid movement in a microfluidic system; Kopf-Sill et al. (U.S. Pat. No. 5,160,702) teaches an analyser with improved rotor structure; and Gordon (U.S. Pat. No. 5,892,577, U.S. Pat. No. 6,256,088, U.S. Pat. No. 6,339,473) teaches an apparatus and method for carrying out analysis of samples.

Devices with the ability to regulate fluid flow through the use of valves are known in the prior art, and differ in their ability to provide real-time control and analogue adjustment of the fluid flow. As an example, some valves have the ability to regulate fluid flow in an analogue manner, like hot water taps, some valves switch between on-off states and vice versa, like irrigation actuators, some valves have a single on-off transition, like electrical safety switches, or off-on-transition, like safety valves in pressurized circuits.

Prior art microfluidic valve devices suffer from the drawback of high cost per valve, as well as the integration scale and complexity that can be achieved. Unfortunately, the reliability of most prior art devices within the meso-scale range is suspect. Further, alteration of sample material by the components of the valve and function of the valve has contributed to their unreliable nature and failure to produce a micro-analytical device with reproducible results. The design of prior art valving devices makes their manufacturing cost and complexity unsuitable for their cost effective use within micro-analytical devices that are "throw-away" and mass produced.

A summary of some of the prior art valve devices is as follows: Unger et al. U.S. Pat. No. 6,408,878 (Unger) teaches elastomeric valve and pump systems wherein a second elastomeric layer is bonded onto a top surface of the first elastomeric layer such that a control channel forms in the second recess between the first and second elastomeric layers and the first elastomeric layer is positioned on top of a planar substrate such that a flow channel forms in the first recess between the first elastomeric layer and the planar substrate. Unfortunately, Unger suffers from complexity of design and cost of manufacturing. In addition to the complexity of the valve, a control system based on pneumatic actuators has to be connected to the various valves through multiple independent lines, and its multiplexing (required in order to have fewer control lines than actual valves on the devices) has impact on the circuit design and requires accurate pressure control.

A patent to Kellogg et al. U.S. Pat. No. 6,302,134 (Kellogg) teaches a heat-activated wax valve in a microfluidics array. This heat-activated wax valve within microsystem platforms requires numerous microfluidics components such as resistive heating elements, temperature sensing elements, mixing structures, to form these heat activated wax sacrificial valves. Apart from a significant occupancy of surface on the microfluidic circuit, the valve of Kellogg further requires an electronic spindle designed rotor capable of transferring electrical signals to and from the microsystem platforms. The requirements and complexity of the Kellogg valve make it impractical to use within micro-analytical systems. Further, the waste from valve actuation can contaminate samples of interest. In addition, the heat is transferred to the wax initially clogging the capillary by heat conduction. In this manner, the heat is also unavoidably transferred to the chip and to the fluids by conduction and convection. This is undesired in most biological applications where the samples could be significantly degraded by heat.

A further prior art valving systems can be found in Kellogg et al. U.S. Pat. No. 6,143,248 (Kellogg '248). Kellogg '248 teaches a capillary microvalve that requires centripetal acceleration to drive fluid in micro-fluid system. The valving device of Kellogg '248 can only be used in a device having centripetal acceleration and also suffers from difficulty in its manufacture.

Another prior art device Kellogg et al. US2002/0097632A1 (Kellogg Application) discloses a bi-directional flow centrifugal microfluidic devices. The valve within the Kellogg Application particularly provides microsystem platforms for achieving efficient mixing of one or a plurality of fluids on the surface of the platform when fluid flow is motivated by centripetal force produced by rotation. This bi-directional flow system is restricted in its use to mixing systems within centripetally driven micro-analytical systems.

Numerous other prior art devices have attempted to improve upon valving devices for micro-analytical platforms, such as Onishi et al. (U.S. Pat. No. 5,547,472) that teaches a catheter with medicament injection pores; Derand et al. (WO00102737A1) (Derand), which teaches polymer valves. An important feature of the polymers used in the valves of the Derand is that they switch from a swelled state to a contracted state or vice versa in a reversible manner, making the choice of the polymer (and its biocompatibility) restricted to a specific class of materials. In addition, the plug is foreseen to be within a capillary, making the manufacturing of the device more expensive and less suitable for mass production since each valve has to be manufactured and positioned within the circuit.

Larsson et al. (WO99/58245) discloses a microfluidic device where the flow of fluids is controlled by different surfaces of the device having different surface characteristics; McNeely et al. (US 2002/0033193) discloses remote valving for microfluidic flow control, Williams (US 2001/0054702A1) teaches a valve for use in microfluidic structures and Parce et al. (U.S. Pat. No. 6,379,974) teaches microfluidic devices and systems utilizing electrokinetic material transport systems to selectively control and direct the transport of materials. Unfortunately, all suffer from complexity of their control systems, design, reliability, high manufacturing costs and application limited to given type of fluids.

Another approach within prior art devices is shown in Limon et al. U.S. Pat. No. 5,869,002 (Limon) where an analysis card containing two mutually separate chambers separated by a frangible partition that is arranged within the analysis card and made of an absorbent and preferably plastic material for absorbing light energy having at least a predetermined wavelength and converting it into heat energy capable of removing the frangible partition thus causing fluid communication between the chambers. Unfortunately, Limon suffers from several deficiencies. The valve of Limon is restricted to a certain configuration that is not adaptable to numerous micro-analytical platforms. More importantly the light energy required within Limon is of such intensity and duration that alteration occurs to the fluids or sample of interest within the adjoining chambers. To overcome the alteration, Limon et al. teach the use of cavities around the frangible partition, to preserve the liquid or liquids circulating in the analysis card from any premature or excessive heating. The valving device of Limon also suffers from its inflexibility in configuration and lack of adaptability to various micro-analytical platforms such as rotating disks or meso-scale devices. Unfortunately, the configuration required by Limon is not adaptable to an economical manufacturing process.

Another drawback of prior art microfluidic circuits has been the difficulty to reconcile flexibility, in the form of fully programmable and configurable devices, with simplicity, in the form of manufacturing and operation. To regulate the flow of fluids through a microfluidic circuit, valves were provided. Prior art methods either rely on active components that can only be provided in limited numbers for reasons of cost and ease of manufacturing, or on passive components that cannot be actuated independently and additionally may depend on characteristics of fluid or the sample of interest. Many active valve systems in the prior art are also characterized by a control system that has to be physically connected to the device, which is often not miniaturized (like the pressure control assembly of the Topaz Crystallizer by Fluidigm Corporation, San Francisco, Calif.) and therefore increases significantly the device complexity, system integration and portability.

A significant drawback of prior art microfluidic circuits has been the difficulty in the handling of biological samples. Prior art devices suffer from valving components that may contaminate the sample of interest, alter or destroy such sample.

Some of the prior art micro-valves integrated in a microfluidic circuit occupy a large surface of the chip. This is at the expense of the other functional components of the device, making the circuit integration (number of components per unit surface) smaller and therefore the chips more expensive. This need to occupy a large surface detracts from their use within a microfluidic circuit.

Another drawback of prior art microfluidic circuits has been the reliability of valving components. Prior art devices suffer from occasional failure and most importantly the lack of feedback controls to recognize such failures. While this aspect may be neglected in chips with a moderate number of valves, (e.g. chips of small complexity), the need of high integration of microfluidic devices requires a higher reliability than the prior art offers of the basic functional components and in particular of valving devices.

A further drawback of prior art microfluidic valves consists in narrow manufacturing tolerances on geometry, surface properties, choice of materials, and complexity of production process. Increasing the integration scale (number of valves in a device) for a manufacturing process which is either complex or has tight tolerances or both results in a high production failure rate, further driving up the cost of production.

Another aspect particular to microfluidics consists in the required disposability of the valves and the overall circuitry. It is well known in the art that the surface-to-volume ratio increases with decreasing volumes. Since a large fraction of the sample is in contact with the chip and valve surfaces, it also means that the fluids contamination is a bigger issue than in the macro-scale world. To avoid contamination of sample, a valve should be preferably used with a single type of sample, and possibly only once to avoid changes in the sample concentration. A valving method relying on reusable valves is therefore less attractive in most microfluidic applications.

The present invention meets the need for a flexible, reliable and yet a simple means to regulate fluid flow, as well as a variety of other needs.

SUMMARY OF THE INVENTION

The present invention is directed towards a microfluidic circuit in which fluid flow is regulated by putting two microfluidic components that are initially separated into fluid communication. Both the time at which the two components are connected and the position of such fluid communication are arbitrary and can be determined externally. Accordingly, the invention describes an infinite number of preferably irreversible valves, all of which are initially in the closed state, but may be opened at any time and in any order.

When a valve is closed, the fluid is contained in a first microfluidic component. As soon as the valve is opened, fluid communication is enabled to at least one or more additional microfluidic components. Whether the fluid will flow into the additional components, to what extent and at which speed, depends on the forces acting on the fluid and the impediments to fluid flow through valving components.

In microfluidic circuits, fluid transport may be achieved through the use of mechanical micropumps, electric fields, application of acoustic energy, external pressure, or centripetal force. A valve according the invention is independent of the mechanism for fluid transport and is therefore compatible with, but not limited to, any of the above means for fluid transport. In general, the inventive valves may be opened, but preferably not closed. This feature is relatively less important for microfluidic circuits where the direction of the force is irreversible, such as is the case for devices exploiting the centripetal force, and can be overcome in most other cases by a suitable design of the circuit and of its basic components.

It is contemplated within the scope of the invention that in order to "close" the inventive valve a two-component "glue" can be distributed to the opposite sides of the opened valve. The glue is chosen among those that do not require mixing of the two components, and have a reasonably fast setting time in order to seal the valve opening. The glue can be acrylic glue commercially available as V5004 by Permabond, which has good flowing characteristics and is non-stringing. It is further contemplated within the scope of the invention that another "glue" having the advantage of biological compatibility, such as fibrin glue or the like may be used to seal an opened valve. A fibrin glue such as tissuecol is contemplated within the scope of the invention. The fibrin glue contains two components that include a fibrin protein on one side and thrombin on the other side. Their contact produces a coagulant reaction that seals the valve.

It is also contemplated within the scope of the invention that fluid passage can be arrested by opening a valve allowing fluid to enter one branch of a Tesla valve. The latter is a fluidic diode or a valvular conduit, that allows easy flow in one direction but in the other the flow gets hung up forming eddies, or counter-currents that stop the flow as surely as if a mechanical valve were moved into the shut position. With this configuration, opening a valve according to the present invention allows fluid to enter in one of the branches and thereby stop fluidic flow, which is the same functionality achieved by the action of closing a valve.

As another example, the inventive valve can be used to distribute a fluid changing significantly the surface properties of a channel (for example, making it more or less hydrophobic). This could produce, as a net effect, the consequence that another fluid (for example water) does not enter the output channel anymore, and the output channel could be considered as "closed" for what concerns the passage of water.

Accordingly, in one aspect of the present invention, an apparatus for processing biological or chemical fluids includes a first substrate comprising a plurality of first meso-scale fluidic components, a second substrate comprising a plurality of second meso-scale fluidic components corresponding to the first meso-scale fluidic components. It is contemplated within the scope of the invention that the inventive apparatus may further comprise additional substrate layers. According to the invention, these additional substrate layers can contain a plurality of fluidic channels, chambers and manipulative components such as lenses and filters.

Between each substrate layer, a material layer or perforation layer separates the plurality of first meso-scale fluidic components from the plurality of second meso-scale fluidic components or additional nano-scale or meso-scale components. The structure of the material layer could be homogeneous or heterogeneous, for example including multilayer and coatings. According to the invention the material layer or perforation layer is comprised of a polymeric compound such as Poly(methyl methacrylate), hereafter referred to as PMMA. It is contemplated within the scope of the invention that other materials such as Low Density Polyethylene (LDPE), Linear Low Density Polyethylene (LLDPE), High Density Polyethylene (HDPE), Polyethylene Teraphathalate (PET), Polyethylene (PE), polycarbonate (PC), Polyethylene Terephthalate Glycol (PETG), Polystyrene (PS), Ethyl Vinyl Acetate (EVA), polyethylene napthalate (PEN) or the like can be used. These polymers can be used singularly or in combination with each other. The use of polymers is preferred because of its ease of use and manufacturing. It is clear that other options, for example metallic foils with or without additional surface treatment, are possible, the choice being connected with the type of electromagnetic radiation generating means used in the application.

The material layer may further comprise optical dye or other like material or layers having adsorptive properties of pre-selected electromagnetic radiation. The absorption can occur through known modifications as those used in absorbing light filters, for example including metallic foils or modifying the surface optical characteristics (n refraction index and k extinction coefficient) or by means of other surface properties like roughness, in such a way that a sufficient amount of pre-selected electromagnetic energy is absorbed with the consequence of perforation. Other technologies can make use of light absorbing globules, for example carbon-black particles, dye emulsions, nanocrystals. In addition, reflective layers, polarization changing layers, wavelength shifting layers could be used to enhance the effective absorption of electromagnetic energy.

An advantage of the current invention consists in the extreme compactness of the valve in the microfluidic circuit that allows maximizing the surface used for fluid storage, incubation and reactions to occur. The valve size, by tuning the optical system position, power and pulse duration of the electromagnetic radiation generating means, can be also adapted to the circuit in a wide range of dimensions, down to the diffraction limit or below. When laminar flow is desired within the microfluidic circuit, the valve cross section should approximately match the cross section of the capillaries that are interconnected. When mixing is desired, valves with a cross section largely different from the fluidic cross section of the circuit are preferable, in order to allow turbulences to act as active mixing agents.

The valves of the present invention are intrinsically low-cost; in particular they have null marginal cost since the cost of the device does not depend on how many valves are implemented on the circuit itself.

The valves according to the invention have a dead volume that can be neglected in microfluidics applications, and is smaller than most other valve designs in the prior art. The inventive valve is typically easy to open, to implement and to build, both in laboratory devices and industrial manufacturing production.

The inventive valve can be extremely fluid tight, by choosing a material layer having low permeability. This allows using the inventive valve as seals for storage of chemicals. Many valving systems, for example those based on hydrophobic breaks, or based on calibrated capillary tension forces on the fluid, or based on pressure actuated modifications of the polymer shape, do not provide enough tightness to vapours and liquids to make the storage possible.

The valve of the invention could be also used for the storage of lyophilised molecules, and for example proteins. In fact, the partial permeability of the material layer to water vapour, could be used in order to control the loss of water vapour by sublimation of a frozen compound, when the disk is heated in vacuum. This would allow long-term storage of molecules, for example pharmaceutical compounds, in very small volumes and ready for use. The molecules could be collected by having a solvent, through a valve opened in the material layer, dissolving the molecules and then exiting the storage cavity by means of a second valve on the layer.

According to the invention, an electromagnetic generating means for generating electromagnetic radiation for directing onto the material layer or perforation layer at a position corresponding to a portion of the material layer located between at least a pair of corresponding meso-scale fluidic components from the plurality of first meso-scale fluidic components and the plurality of second meso-scale fluidic components. The electromagnetic generating means allows perforation of the material layer at a position allowing fluid communication between the pair of meso-scale fluidic components. The perforation of the material layer occurs in a defined manner that is dependent on the wavelength and intensity of the radiation, which is applied to the device within a limited space and time, thereby avoiding any substantial alteration of fluids or samples of interest.

In another aspect of the present invention, an apparatus for multiplexing biological or chemical fluids includes a first substrate comprising a set of input capillaries, a second substrate comprising a set of output capillaries corresponding to the set of input capillaries, a layer of material positioned between the first substrate and the second substrate forming an interface between each of the input capillaries and each of the output capillaries corresponding thereto and electromagnetic radiation generating means for generating electromagnetic radiation for directing onto the material layer at the interface between a first input capillary of the plurality of input capillaries and a corresponding first output capillary of the plurality of output capillaries. The electromagnetic generating means allows perforation of the material layer at the interface allowing first input capillary and the first output capillary to be in fluid communication without damage or substantial alteration to the biological sample or fluids within the microfluidic network.

The multiplexing capability addresses the need of a flexible, programmable fluid handling. The choice of the fluids involved in a reaction, for example, can be made in real-time during protocol execution.

In yet another aspect of the present invention, an apparatus for volumetric quantitation of a liquid in a centripetal device includes a first meso-scale fluidic component containing a liquid for quantitation, a second meso-scale fluidic component and fluid communication means for placing the first and the second fluidic components in fluid communication at a first position. Upon a centripetal force or other force being placed on the liquid, a first amount of the liquid left in the first fluidic component or a second amount of liquid transferred to the second fluidic component is determined by the choice of the first position.

In another aspect of the present invention, a method for volumetric quantitation of a liquid in a centripetal device includes loading a liquid in a first meso-scale fluidic component, enabling fluid communication at a first position between the first fluidic component and a second meso-scale fluidic component, spinning the centripetal device to cause a portion of the liquid to be transferred from the first fluidic component to the second fluidic component and determining a first amount of liquid left in the first fluidic component or a second amount of liquid transferred to the second fluid component.

This method has the advantage of an arbitrary volume to be quantified, without being bound to discrete steps in the dosing volume.

In another aspect of the present invention, a method for separating a fluid into its fractions makes use of the centrifugation occurring during the rotation to separate the medium into its constituting fractions by determining the choice of the perforation position.

In still yet another aspect of the present invention, a method of moving a liquid sample in a centripetal device from an outer radial position to an inner radial position includes loading a buffer liquid in a first meso-scale fluidic component, loading a liquid sample in a second meso-scale fluidic component, enabling gas-tight fluid communication between the first meso-scale fluidic component and the second meso-scale component across a fluidic circuit sealed on one end by the buffer liquid and on the other end by the liquid sample, enabling the buffer liquid to exit the first fluidic component and spinning the centripetal device to cause the buffer liquid to exit the first fluidic component. Movement of the buffer liquid exiting the first fluidic component forces the liquid sample from an outer radial position to an inner radial position.

In a further aspect of the present invention, a method of performing a washing step in a centripetal device by moving a liquid sample from an outer radial position to an inner radial position includes loading a buffer liquid in a first meso-scale fluidic component, loading a liquid sample in a second meso-scale fluidic component, enabling gas-tight fluid communication between the first meso-scale fluidic component and the second meso-scale component across a fluidic circuit sealed on one end by the buffer liquid and on the other end by the liquid sample, enabling the buffer liquid to exit the first fluidic component and spinning the centripetal device to cause the buffer liquid to exit the first fluidic component. Movement of the buffer liquid exiting the first fluidic component forces the liquid sample from an outer radial position to an inner radial position.

In still yet another aspect of the present invention, a method for determining a polar position and a radial position of a pickup in a reference frame of a rotating device includes detecting a first marker on the device by means of a pickup, detecting a second marker on the device by means of the pickup, wherein an angular distance from the first marker to the second marker is a continuous or discontinuous, derivable or non-derivable, non-constant function of a radial position of the pickup, recording the time elapsed between the detection of the first marker and the second marker, determining a radial position of the pickup from the elapsed time and a rotation period of the rotating device and determining a polar position of the pickup a first time using the difference between the first time and a second time corresponding to the detection of a marker and the rotation period of the rotating device.

In another aspect of the present invention, a method for determining a polar position and a radial position of a pickup in a reference frame of a rotating device includes recording a first time at which a pickup detects a first marker on a rotating device, recording a second time at which the pickup detects a second marker on the device, wherein an angular distance from the first marker to the second marker is a continuous or discontinuous, derivable or non-derivable non-constant function of a radial position of the pickup, determining the radial position of the pickup from the difference in time between the second time and the first time and a rotation period of the rotating device and determining a polar position of the pickup at a third time using the difference between the third time and a fourth time corresponding to the detection of a marker and the rotation period.

In yet another aspect of the present invention, a method for processing biological or chemical fluids includes providing a first substrate comprising a plurality of first meso-scale fluidic components, providing a second substrate comprising a plurality of second meso-scale fluidic components corresponding to the first meso-scale fluidic components, providing a layer of material separating the plurality of first meso-scale fluidic components from the plurality of second meso-scale fluidic components, directing electromagnetic radiation onto the layer at a position corresponding to a portion of the layer located between at least a pair of corresponding meso-scale fluidic components from the plurality of first meso-scale fluidic components and the plurality of second meso-scale fluidic components and perforating the material layer at the position, wherein the perforation of the material layer allows fluid communication between the pair of meso-scale fluidic components without damage or substantial alteration of any fluid or sample of interest within such microfluidic network.

In another aspect of the present invention, a processing disk for processing biological or chemical fluids includes a first substrate comprising a plurality of first meso-scale fluidic components, a second substrate comprising a plurality of second meso-scale fluidic components corresponding to the first meso-scale fluidic components, and a layer of material separating the plurality of first meso-scale fluidic components from the plurality of second meso-scale fluidic components.

These and other advantages, objects and features of the invention will be apparent through the detailed description of the embodiments and the drawings attached hereto. It is also to be understood that both the foregoing general description and the following detailed description are exemplary and not restrictive of the scope of the invention.

BRIEF DESCRIPTION OF THE DRAWINGS

The foregoing and other features and advantages of the present invention will be more fully understood from the following detailed description of illustrative embodiments, taken in conjunction with the accompanying drawing in which:

FIGS. 5C, 5D, 5E, 5F and 5G illustrate the self metering embodiment according to the invention wherein a sample to be metered is with sample metering chamber containing a meniscus allowing for the metering of a known quantity within a subsequent sample chamber;

DETAILED DESCRIPTION OF THE INVENTION

Figure 1A:
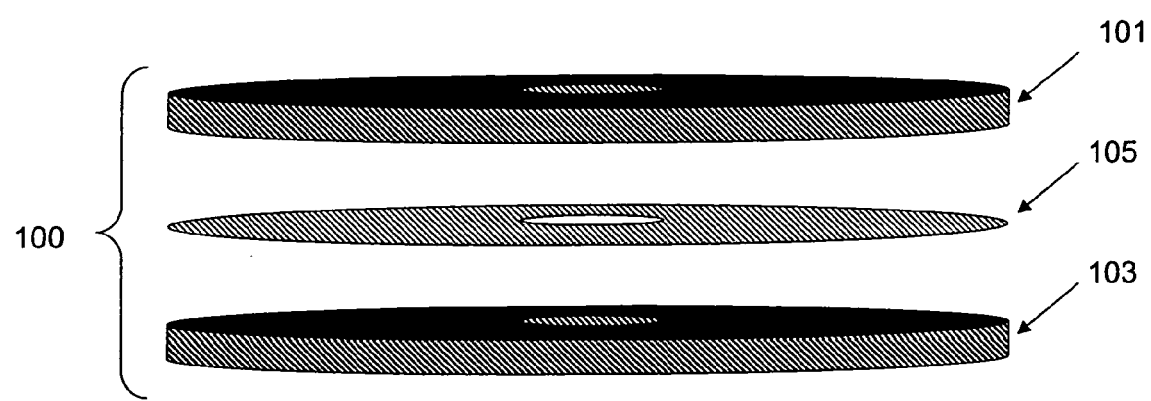
FIG. 1A illustrates the components comprising the disk according to the invention.

The present invention provides centrifugal rotors and Microsystems and in particular nano-scale or meso-scale microfluidic valve technology platforms as well as a number of its applications for providing centripetally-motivated fluid micromanipulation. For the purpose of illustration, the drawings as well as the description will generally refer to centripetal systems. However, the means disclosed in this invention are equally applicable in microfluidic components relying on other forces to effect fluid transport.

For the purposes of this specification, the term "sample" will be understood to encompass any fluid, solution or mixture, either isolated or detected as a constituent of a more complex mixture, or synthesized from precursor species. A sample may further be comprised of a suspension or an emulsion containing beads, nanoparticles, globules, cells, or the like.

For the purposes of this specification, the term "in fluid communication" or "fluidly connected" is intended to define components that are operably interconnected to allow fluid flow between components. In illustrative embodiments, the micro-analytical platform comprises a rotatable platform, such as a disk, or experimental microfluidic chips whereby fluid movement on the disk is motivated by centripetal force upon rotation of the disk and fluid movement on the experimental chip is motivated by pumps and fluid communication is achieved by the perforation of a material layer.

For the purposes of this specification, the term "material layer" or "perforation layer" is intended to define components that separate various micro fluidic components such as chambers, channels and other microfluidic elements and upon perforation by electromagnetic irradiation bring such micro fluidic components in fluid communication with each other.

For the purposes of this specification, the term "biological sample", "sample of interest" or "biological fluid sample" will be understood to mean any biologically-derived or synthesized analytical sample, including but not limited to blood, plasma, serum, lymph, saliva, tears, cerebrospinal fluid, urine, sweat, plant and vegetable extracts, semen, or any cellular or cellular components of such sample.

For the purposes of this specification, the term "perforation" is intended to define the dissolution of a portion of any such material layer or perforation layer either by decomposition or phase change (into a different solid aggregation, liquid, gas or plasma states) or chemical uncoupling of any such material forming such perforation or material layer. Such perforation is achieved by electromagnetic irradiation having an energy and wavelength meant to be absorbed by such material layer or additives contained within or adjacent to such material layer with the consequence of creating a passing through hole in the layer.

For the purposes of this specification, the term "ablation" specifically refers to a rapid process where the heat wave ejects the material that is vaporised into plasma.

For the purposes of this specification, the term "mesoscale", or "nano-scale" will be understood to mean any volume, able to contain fluids, with dimensions preferably in the sub-micron to millimetre range.

Representative applications of centripetal systems (e.g., centrifuge) employ circular devices, with the rotation axis at their centre. For the purpose of illustration, the drawings, as well as the description, will generally refer to such devices. Other shapes, including elliptical and rectangular devices, irregular surfaces and volumes, and devices for which the rotation axis does not pass through the centre, may be beneficial for specific applications.

The microfluidic device used for illustrative purposes in the present invention will be referred to as a disk which, in some embodiments, is rotating around a given axis. The operations that may be performed depend on the shape, the material composition and the complexity of the disk. The microfluidic system may include, in addition to the disk, one or more than one external moiety designed to perform operations on the disk, including but not limited to the loading of chemical, biological or biochemical fluids, the optical readout of signals, the detection of radioactivity, the analysis of assays, detection of compounds of interest, injection of samples from the disk to a chromatographer or mass spectrometer, exposure of the disk to x-ray or gamma or neutron beams, transfer of fluids to or from the disk, transfer of fluids from a disk to another disk.

In an illustrative embodiment of the present invention, the external moiety includes a pickup, a device capable of focusing a substantial amount of electromagnetic radiation onto a point in the disk, and a spinning device. The disk and the pickup are designed to interact primarily by means of electromagnetic radiation, at a pre-selected preferred wavelength or spectrum of wavelengths. Hereafter, this wavelength or spectrum of wavelengths will be referred to as the "pickup wavelength" or "pre-selected wavelength".

In one aspect of the present invention, a novel system for valve implementation in a microfluidic circuit is presented. It represents a fully programmable (active) solution where the fluid flow is controlled by means of a distributed valve system, meaning that the position of a given valve is arbitrary and the valves themselves extend to the full microfluidic circuit. The described valves are typically limited to a closed-to-open transition, even if schemes that restore a valve state from open to close are possible and here commented. Another significant advantage of the system is the large number of valves that may be integrated in a circuit.

The Disk

The preferred embodiment of the disk includes a circular microfluidic device. Rectangular disks, rotating around an axis that preferably does not intersect the disk volume, offer specific advantages. To achieve compatibility with commercial products related to compact disk technology, the disks may have similar or identical dimensions thereto. Likewise, rectangular disks, with a footprint equal to that of micro well plates or of credit cards, are particularly suited for automatic handling and storage of compounds, including the transfer of fluids between disks and the transfer of fluids from disks to standard well plates used in the chemical and biochemical industry, as well as from standard well plates to disks.

As shown in FIG. 1A, the internal structure of the disk 100 in one illustrative embodiment comprises a sandwich of at least three layers: a top side 101, a bottom side 103, and a material layer 105 separating the two sides 101, 103. To achieve higher densities in a single disk, the sandwich structure can be replicated to produce a multi-base sandwich. In such a configuration, sides 101, 103 are contained between at least two material layers 105 and have microfluidic components on both surfaces, and possibly comprise additional microfluidic elements putting into fluid communication the components at their respective surfaces.

Figure 1B:
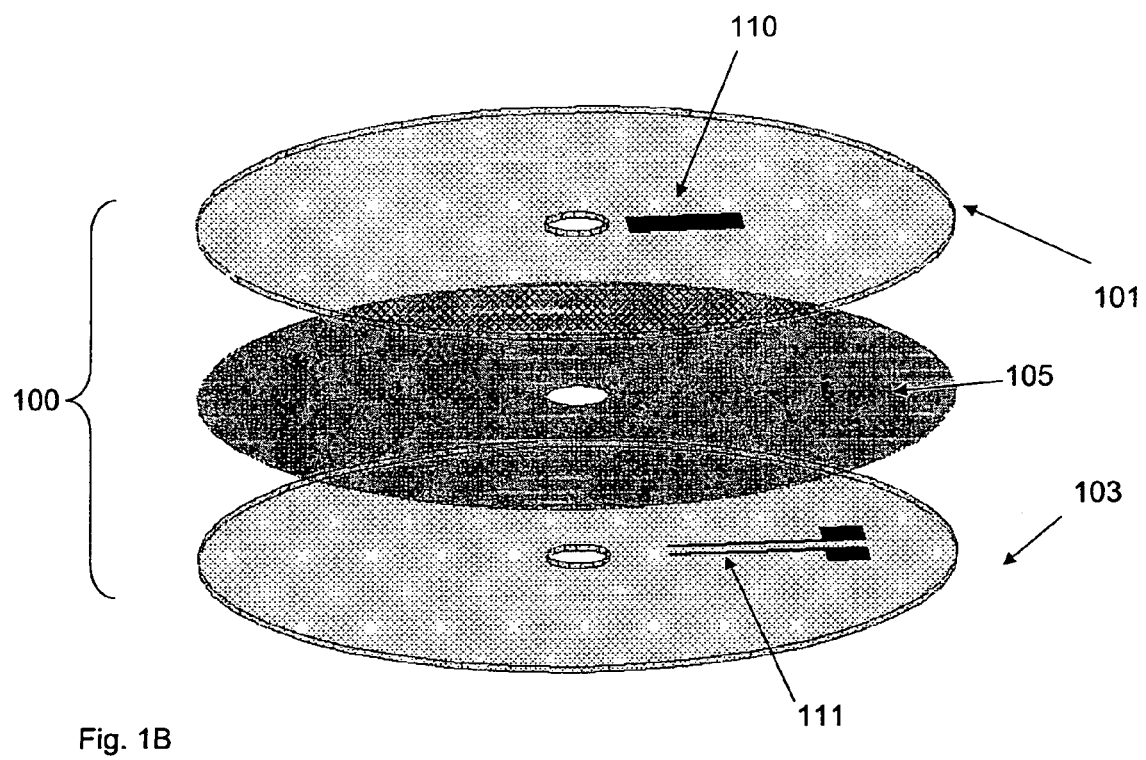
FIG. 1B illustrates the components comprising the disk according to the invention microfluidic components on both sides of the material layer are shown in a possible configuration.
Figure 2A:
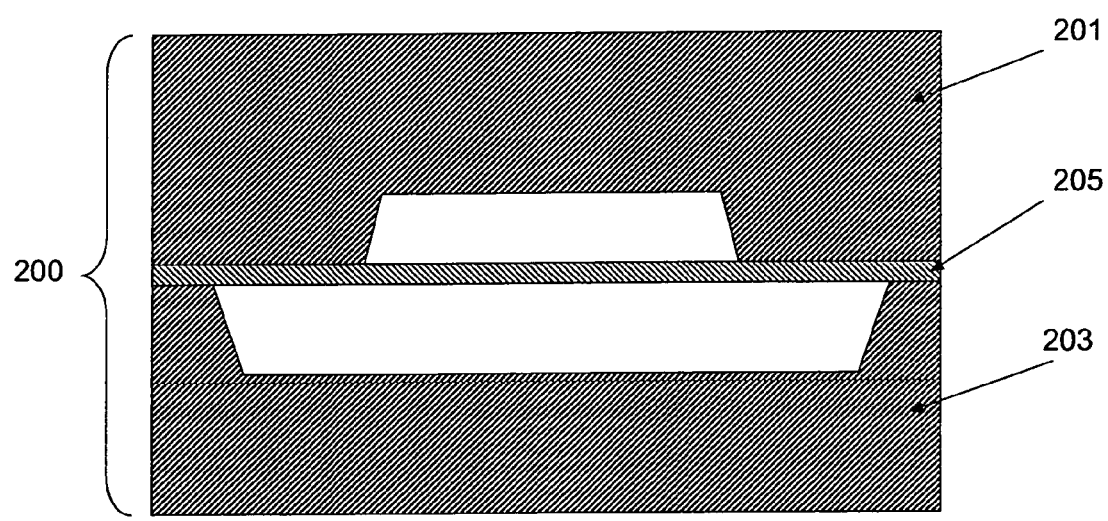
FIG. 2A illustrates a section of the inventive disk wherein microfluidic components within each top and bottom side are separated by a material layer.
Figure 2B:
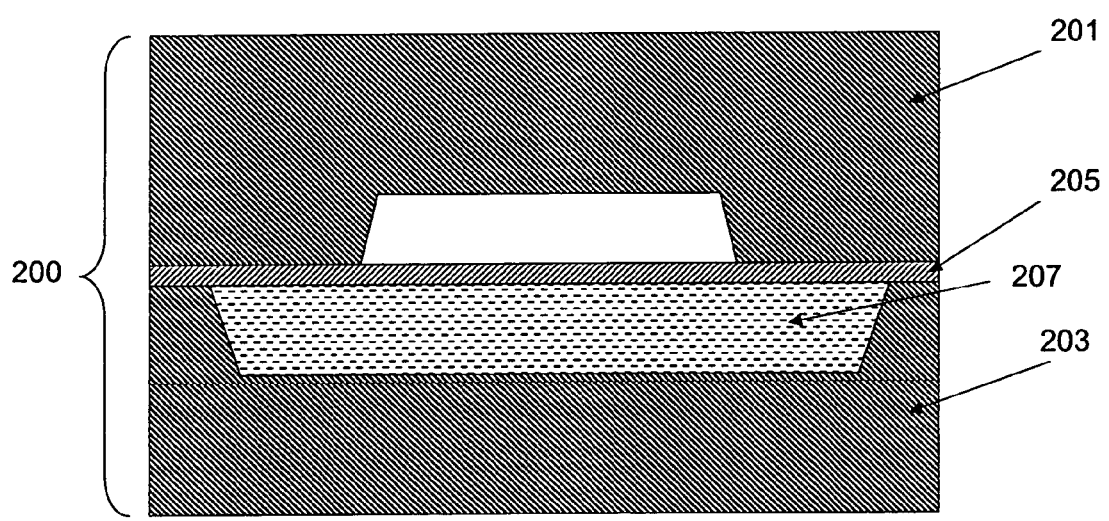
FIG. 2B illustrates a section of the inventive disk wherein microfluidic components within each top and bottom side are separated by a material layer and the bottom side microfluidic component contains a fluid or sample.
Figure 2C:
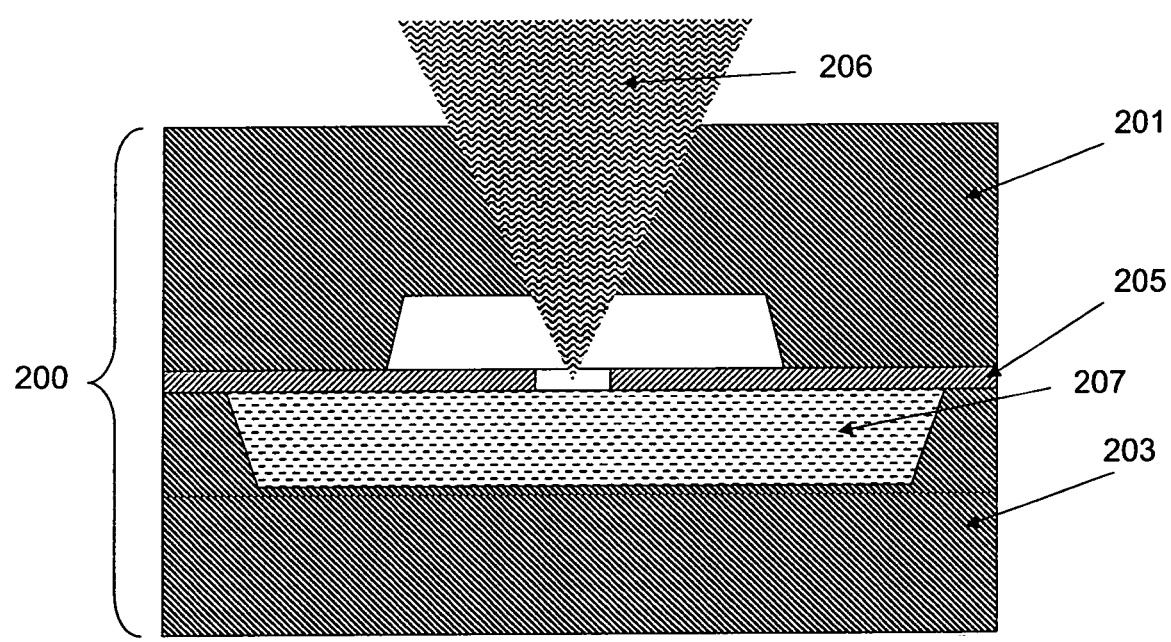
FIG. 2C illustrates a section of the inventive disk wherein microfluidic components within each top and bottom side are separated by a material layer and the bottom side microfluidic component contains a fluid or sample and the material layer is perforated by electromagnetic radiation.
Figure 2D:
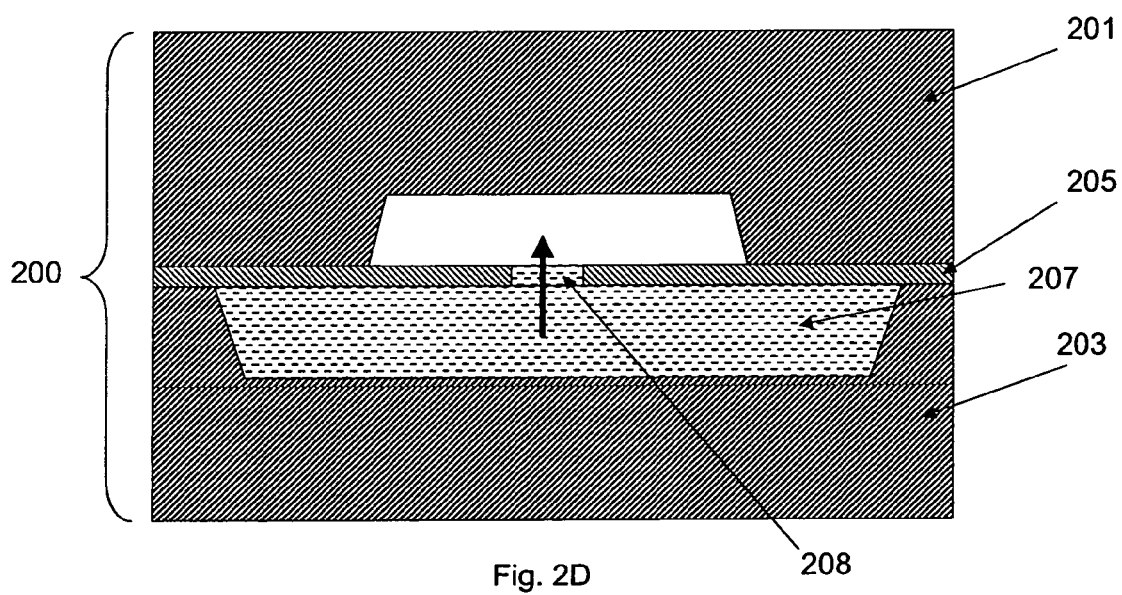
FIG. 2D illustrates a section of the inventive disk wherein microfluidic components within each top and bottom side are separated by a material layer and the bottom side microfluidic component contains a fluid or sample and the material layer is perforated by electromagnetic radiation and the sample moves through centripetal forces from the bottom microfluidic chamber to the top microfluidic chamber.
Figure 2E:
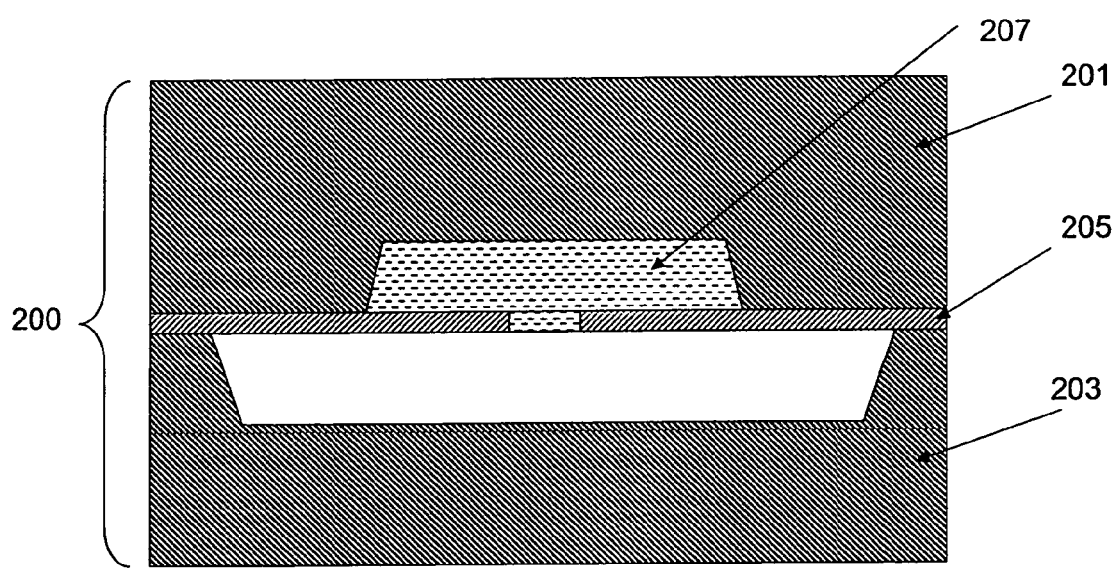
FIG. 2E illustrates a section of the inventive disk wherein microfluidic components within each top and bottom side are separated by a material layer and the bottom side microfluidic component contains a fluid or sample and the material layer is perforated by electromagnetic radiation and the sample moves through centripetal forces from the bottom microfluidic chamber to the top microfluidic chamber.

Turning to FIG. 1B the disk according to the invention is shown wherein the top side 101 contains a microfluidic structure 110 (which is a dosimeter reservoir described below) and the bottom side 103 contains a corresponding microfluidic structure 111 (which is the capillary outlets of the dosimeter). Numerous microfluidic structures can be incorporated within the top side 101 and bottom side 103. These microfluidic structures are separated by the material layer 105 and can be place in fluid communication with each other by the perforation of the material layer 105. The microfluidic structures 110, 111 contained within the respective top and bottom sides 101, 103 may be mirror images of each other or they may be dissimilar structures separated by the material layer 105 having an integrated function with each other upon perforation of the material layer 105.

A. Material Layer

A variety of materials are suitable for the material layer 105 or perforation layer, including but not limited to thin polymer foils and metallic foils. The thickness in microfluidic applications typically varies between about 0.5 to about 100 microns, depending on the material properties and on the characteristics of the pickup.

In a first illustrative embodiment infrared absorbing polymer foils are used since they can be easily perforated with simple and economical means. These polymer foils are comprised of a polymeric compound such as Poly(methyl methacrylate), Low Density Polyethylene (LDPE), Linear Low Density Polyethylene (LLDPE), High Density Polyethylene (HDPE), Polyethylene Teraphathalate (PET), Polyethylene (PE), polycarbonate (PC), Polyethylene Terephthalate Glycol (PETG), Polystyrene (PS), Ethyl Vinyl Acetate (EVA), polyethylene napthalate (PEN) or the like can be used.

It is contemplated within the scope of the invention that these polymeric compounds may be used singularly or in combination with each other. In a further illustrative embodiment copper foils with a thickness in the order of about 2 microns are can be used. Copper foils are routinely produced for applications in the electronic industry, specifically for printed circuit boards. Thin metallic foils, such as copper, exhibit a natural absorption in the domain of ultraviolet light wavelength, which is of interest in some of the illustrative embodiments.

It is further contemplated within the scope of the invention that additional materials may be used for the material layer 105 such as waxes, because of their low melting point, and polysaccharides such as cellulose, or the like. It is also contemplated within the scope of the invention that liquid crystal polymers may be used for the material layer.

The choice of material layer 105 is dictated by the requirement for large light absorption at the pickup wavelength. Except for the choice of material, large absorption may be achieved by modifying the optical properties of any such material using dyes, coatings, surface treatments or by an appropriate multi-layer construction to exploit light interference processes. It is contemplated within the scope of the invention that dyes having desired optical properties such as ADS905AM, an infrared dye from American Dye Source Inc. of USA, whose chemical formulation is $C_{62}H_{96}N_6SbF_6$ or the Epolight 2057, an infrared dye from Epolin Inc. of USA whose absorption spectrum is suitable to near infrared sources, can be loaded into the material layer. It is further contemplated that infrared absorbing solutions such as Epolight 2180, Epolight 2189, and Carbon black loading, either in homogeneous dispersion or in heterogeneous suspension or emulsion (globules or particles) can be used. It is also contemplated within the scope of the invention that other absorption spectrums below or above infrared may be used to match the material layer 105 with any form of electromagnetic radiation.

In one illustrative embodiment a material layer 105 is formed from PMMA and loaded with the infrared dye ADS905AM in a weight percent of approximately 0.5%. The dye is suspended within the PMMA film in non-uniform globules. While the suspension of such dye is not distributed uniformly throughout the material layer, it is sufficiently distributed to produce a desired absorption of the pre-selected wavelength.

It is further contemplated within the scope of the invention that other dyes such as Epolight 2057, Epolight 2180, Epolight 2189 or the like may be used to achieve a desired spectral absorption. It is also contemplated within the scope of the invention that other compounds other than dyes such as Carbon black, or the like, having light absorption properties may be used to achieve a desired spectral absorption.

Additional requirements for the material layer 105 depend on the application, and relate specifically to the interaction of fluids with neighbouring materials. Examples of additional requirements are resistance to corrosion, prevention of fluid contamination, absence or presence of catalytic reaction, the build-up of electrical charge and/or the presence of electrical currents, biocompatibility.

Procedures to achieve the permanent connection between the material layer 105 and the two sides 101, 103 include bonding or gluing as known in the art (lamination, hot bonding, UV bonding, plasma treatment of the surfaces, solvent bonding, pressure adhesive, heat adhesives). The bonding procedure may exploit polymer foils treated with thermoset films on both sides. Such foils are commercially available and currently produced for printed circuit boards. In addition, various materials suitable as a base are available off-the-shelf, including carbon-black loaded polyester and black Mylar. In a first illustrative embodiment, the material layer 105 shows no internal structure, obviating the need for any alignment of the material layer 105 with respect to the sides 101, 103.

B. Sides

With continuing reference to FIG. 1, the sides 101, 103 comprise the microfluidic components of the disks, containing the fluids. Depressions within one surface of the substrate forming the sides 101, 103 form the microfluidic components. Meso-scale components and channels, also referred to as capillaries or micro-capillaries, may be provided by a variety of techniques known in the art, including engraving, fluoric acid wet etching, embossing, hot embossing, micro-machining, laser ablation, mechanical machining or polymer moulding.

It is contemplated within the scope of the invention that microfluidic components such as chambers and channels may be formed by the printing of such components upon a substrate, wherein such printed components and substrate form the sides 101, 103 of the inventive disk. The printing of microfluidic structures can be achieved by silk screening printing techniques or other printing techniques known in the art.

Each meso-scale component includes a volume, able to contain fluids, with dimensions preferably in the sub-micron to millimetre range. In an illustrative embodiment, the meso-scale components are understood as open components engraved or printed on the surface of the sides 101, 103 and facing the material layer 105. The sides 101, 103 may further comprise additional fluid connections and components, including dedicated input and output ports to allow the fluids to reach the meso-scale network, instruments, batteries, electrical connections and other instrumentation. Suitable materials for the sides 101, 103 include glass, quartz, monomers, silicon, polymers, acrylic plastics, and polycarbonates, cyclic olefin copolymers (COC). It is contemplated within the scope of the invention that the sides 101, 103 may integrate optical and electrical components, including motors, conductors, chips, lenses and prisms. It is also contemplated within the scope of the invention that the surfaces in contact with the material layer 105 may be modified, in particular to have different optical properties allowing for the focusing of the pickup onto the material layer 105.

It is contemplated within the scope of the invention to have disks with sides totally sealed, where gases in contact with fluids cannot exit from the device. This characteristic can be exploited to handle high toxicity chemicals or radioactive fluids, and allows performing operations with disks in vacuum, or in general when the external pressure is different from the internal pressure (pressurized reactions).

For the purpose of the present invention, the sides 101, 103 forming the disk are substantially transparent or selected portions thereof are transparent to wavelengths of light corresponding to the pickup wavelength. According to the invention optical lenses and optical components may be embedded within the sides 101, 103 to direct a light wavelength to a desired valving area within the microfluidic network. It is contemplated within the scope of the invention that there is a different refraction index of the side with respect to the material layer 105, in order to allow optical detection of the interface surface by reflection of the pickup light emission or for a better compatibility with the fluids present in the microfluidic components.

Additional requirements of the sides 101, 103 depend on the application, including interaction or contamination of the fluids in the device and optical properties affecting the study of the fluids in the device and their reactions. In addition, cost and ease of mass production are also considered.

The Pickup

The pickup includes an optical means to irradiate the material layer or layers of the disk at the pickup wavelength. In one illustrative embodiment, a laser source whose light emission is focussed, by optical elements (for example) and through one side of the disk, onto a focal point located inside the material layer or on the material layer near to it is contemplated. According to the invention, a requirement for the pickup is the ability to concentrate or focus a sufficient amount of electromagnetic energy on a sufficiently small surface area of the base. Accordingly, a basic operation of the present invention is the perforation of the material layer at a specific time and position, induced by irradiation provided by the pickup. The preferred wavelengths for the emission are in the infrared, visible, and ultra-violet parts of the spectrum. Wavelengths within the infrared region are desirable since most biological samples—including cells—and fluids used in the biological domain do not absorb near infrared radiation and therefore are not substantially affected by infrared irradiation.

The laser emission may be achieved by means of compact and low-cost laser diodes, with commercially available diodes spanning a large range of frequencies, starting from and above 375 nm. The largest power available in current laser diodes for commercial compact disk readers is about 200 mW. The highest intensity achieved by this technology is in the near infrared region. In an illustrative embodiment the laser diode used is an OSRAM PL90_3, made by Osram. In yet a further illustrative embodiment the laser diode used is a JDS SDL-6380A made by JDS Uniphase. While the JDS diode has a lower peak power than the OSRAM diode, its better heat dissipation, smaller slit size, narrower far field emission and larger maximum pulse width allows for better performance. It is contemplated within the scope of the invention that other sources such as q-switched lasers, diode pulsed solid state lasers (DPSS), carbon dioxide lasers, Titanium Sapphire lasers fibre lasers, excimer lasers, flash lamps, gas discharge or the like may be used.

According to the invention, the laser diode operates in a substantially pulsed mode. The pulse geometry is selectable to deliver desired energies to intended targets and allows the instantaneous power to be significantly larger, provided that the operational duty cycle is short enough to allow appropriate cooling of the laser junction. Commercial laser diodes with peak power output reaching up to about 70W are available and even higher peak rates are possible with more expensive solutions.

An aspect of using very short pulses is that the minute energy deposited in the base is hardly transferred to the samples and to the surroundings area. The heat wave propagates away from the perforation spot with a finite speed. During a short pulse with high intensity, the outgoing energy flow can be smaller than the ingoing energy flow, the energy remains therefore concentrated in a limited spot, with a steep rise in localized temperature rapidly producing perforation with efficacy.

Optical focusing is typically achieved by a single optical system composed of few optical elements. To achieve optimal collimation and alignment of the beam onto the base, one element may be moved in different directions, for instance by means of electric coils immersed in a magnetic field. Optimisation of the optical path has been made by taking into account the disk exposure requirements. The side's thickness can introduce significant coma and astigmatism, which is sometimes difficult to correct when small spots are envisaged.

In an illustrative embodiment, the optical system is comprised of a f=6 mm MG GLC001 collector lens, a LiteOn CD pickup (NA=0.45) by LiteOn, with a real focus in between the two systems at 25 mm from the CD lens front face. This particular configuration collects onto the base a light intensity of about 16 μJ in about 10 μs exposure. The effective power density of this configuration has proven to be perfectly sufficient for perforation of various material layers. By means of a pinhole and a pyrometer PEM 100 by Lasertechnik Berlin of Germany, it was possible to estimate and optimize the amount of optical energy effectively collimated onto the focal spot onto the base.

The above configuration provides that the pickup structure implemented in commercially available CD devices, with applications in audio, video and computer data storage, may be applied to the present invention, and that focusing the laser onto the base is possible by processing the fraction of light reflected at the base surface with an appropriate optical system.

In another illustrative embodiment, the pickup may contain two or more light sources, only one of which is used to perforate the base. The focusing of the lens and the determination of the pickup position is obtained through a different source which can be a low power, continuous or quasi-continuum (QCW) wave emission. The use of multiple light sources allows choosing a base that absorbs the radiation meant to perforate the base, and reflect the radiation meant to determine the base position through the same optical system.

The pickup device may further include an optical system for determining if the focussing of the electromagnetic radiation onto the base is achieved. For example, partial reflectivity of the base may be used as an optical feedback mechanism if analysed through a Foucault (astigmatic) focussing system. Such a system has been implemented in commercially available optical readers for CD and DVD media.

The pickup in the present invention is similar to devices used to manipulate microscopic objects by means of a focussed light beam. This operation, also known as tweezing, allows one to hold and move single objects using the electromagnetic forces generated by a light wave front, which is substantially convergent or divergent.

It is contemplated within the scope of the invention that the pickup of the present invention may be a device serving one or more distinct purposes including, for example, the control of the fluidic process by perforation of a material layer, tweezing of particles and optical analysis of the samples contained in the microfluidic components. It should be also noted that the pickup does not have contact with the microfluidic device. This potential can be exploited in those applications where contamination has to be absolutely avoided, for example forensic analysis of samples (contamination from the outside to the inside) or handling toxic or radioactive fluids (contamination from the inside to the outside).

Material Layer Perforation to Open a Valve

Microfluidic handling in the present invention is regulated and performed through the dynamic, real-time configuration of a microfluidic network. This configuration is achieved by putting into fluid communication microfluidic components within sides of the disk on opposite sides of a material layer. This connection may be used either by a fluid moving from one microfluidic component to a second one or by two fluids coming into contact in specific places. The former is referred to as a flow valve, the second as contact establishment.

Turning to FIG. 2A-2E, the connection of two or more microfluidic components is shown. To achieve fluid communication, the following operations are performed: The pickup (not shown) or the disk 200 is positioned such that an electromagnetic radiation emission 206 is directed at a position of the material layer 205 where perforation is to occur. This may be achieved by moving either the disk 200, or the pickup, or both; The focusing system, if present, is adjusted to minimize the spot size and concentrate the energy onto the material layer 205 in the position of perforation; Electromagnetic radiation of sufficient intensity is generated by the pickup and directed onto the material layer 205 that is positioned between microfluidic components within the top side 201 and bottom side 203 of the disk 200. The intensity of such radiation, its limited time duration and its limited spatial application prevents or substantially avoids alteration of fluids 207 (or samples) within the microfluidic network. The energy deposition, specifically, the fraction of energy absorbed by the material layer 205, causes perforation (also referred to as drilling) of the material layer 205.

The forces acting on the fluid 207, in a preferred embodiment a centripetal force, cause the fluid 207 to flow from the microfluidic component in one side to the microfluidic component in the other side through the point of perforation 208. The point of perforation 208 and the resulting opening is referred to as a virtual laser valve (VLV). This typically allows the fluid 207 to access the next step or merge with the adjoining fluidic chamber or channel in the microfluidic network.

The drilling of the base or perforation occurs via different physical phenomena, including ablation and melting, or through the breaking or relaxation of molecular bonds. Their relative importance depends on the energy density, the pickup wavelength, the time duration of the pulse, the composition of the material layer, the polarization of the electromagnetic radiation, phenomena of heat dissipation in an irradiated body, the development of plasma waves, and the presence of materials neighbouring the point of perforation zone. Ablation specifically refers to the rapid process where the heat wave ejects the material that is vaporised into plasma. Melting occurs through an intermediate state of liquid phase, unavoidably leading to partial transfer of heat from the illuminated area to the sides.

Both ablation and melting may produce a gas, like $CO_2$, for example, when hitting a polymer, with additional small solid deposits. Both processes are industrially used for a number of commercial applications, including micro-mechanical devices (MEMS), polymer laser drilling and cutting, metal drilling and cutting, and surface treatment by ablation. A substantial and growing experience with excimer lasers, for example by Lambda-Physik, shows that the potential of ultra-violet laser emission may allow achievement of a high quality perforation by direct breakage of the molecular bonds. This type of drilling achieves high resolution and high quality drilling, which may be of substantial benefit to the present invention to achieve a large integration scale of the microfluidic components onto a disk.

Because the perforation volume is small, compared to the dimensions of the microfluidic components in the sides, the overall amount of material scattered by opening a valve is negligible and does not substantially impact or alter fluids in the microfluidic components. The pickup is protected from the blast of material since it occurs within the sides. As described here, the perforation process is generally irreversible: the material layer 205 is removed upon perforation when opening the valve. According to the invention, the material layer 205 generally cannot be recovered to restore the valve to its closed state. Nevertheless, the present invention may be applied to configurations where the valve may be closed. One such configuration includes a case where a polymer in the liquid phase, which can allow the flow of gases, polymerizes at the position of perforation or in another position connected to the circuit in a gas tight manner to impede gas flow or fluid movement. A similar result can be achieved by thermoset materials and fibrin glue, or other 2-components sealing agents. A different implementation of an open-to-close transition makes use of a Tesla valve, which can be opened by opening a valve. The Tesla valve increases the impedance of the fluid flow, effectively achieving the result of blocking the fluid flow in one given direction.

The optical characteristics of the material layer 205 and the sides 201, 203 determine both the modality of energy deposition and the requirements of the electromagnetic radiation provided by the pickup. Material layers 205 formed from polymers are advantageous because of their low enthalpy: the energy required to transform a polymer from the solid to the liquid state is typically smaller than that required in the case of metals. Consequently, smaller energy density is sufficient for perforation. Conversely, the sides 201, 203 should be as transparent as possible at the pickup wavelength, with optical properties such that the focussed pickup emission is not scattered before arriving at the base surface nor absorbed leading to heating up of the side material or adjacent fluids. Effects to be considered include bi-refringence, optical quality of the surface, and uniformity of the optical thickness. Various polymers, including the polycarbonates used in compact disk applications, are substantially transparent in the entire visible spectrum as well as the near infrared, and in addition, show good optical quality of the surfaces.

Components of the invention such as disks, chambers, channels, filters and their respective optical characteristics are advantageously provided having a variety of composition and surface coatings appropriate for a particular application. Component composition will be a function of structural requirements, manufacturing processes, and reagent compatibility/chemical resistance properties, including biocompatibility.

Specifically, components of the invention such as sides are provided that are made from inorganic crystalline or amorphous materials, e.g. silicon, silica, quartz, or from organic materials such as plastics, for example, poly(methyl methacrylate) (PMMA), acetonitrile-butadiene-styrene (ABS), polycarbonate, polyethylene, polystyrene, polyolefin, polypropylene, fluoropolymer and metallocene. Thermoset materials, like SU8 and PDMS are a viable solution. Surface properties of these materials may be modified for specific applications. Surface modification can be achieved by methods known in the art that include but are not limited to silanization, ion implantation and chemical treatment with inert-gas plasmas (i.e., gases through which electrical currents are passed to create ionization). Similar processes could be applied to the material layer for a complete treatment of the surfaces in contact with the fluids.

It is contemplated within the scope of the invention that components of the disk may be made of composites, co-polymers or combinations of these materials, for example, components manufactured of a plastic material having embedded therein an optically transparent glass surface comprising for example the detection chamber of the disk or lenses and mirrors for directing electromagnetic radiation to a valving area within the material layer in order to perforate such layer.

Disks of the invention and their respective components are preferably fabricated from thermoplastics such as Teflon, polyethylene, polypropylene, methylmethacrylate and polycarbonates, among others, due to their ease of moulding, stamping and milling. Alternatively, such components can be made of silica, glass, quartz, or thermoset materials.

A micro analytical fluid handling system according to the invention is fabricated by sequential application of one or more of these materials laid down onto the thermoplastic substrate. Disks of the invention may be fabricated with an injection moulded, optically-clear base layer or sides having optical pits in the manner of a conventional compact disk (CD). It is contemplated within the scope of the invention that other methods of fabrication or manufacture known in the art may be used. It is further contemplated that microfluidic chips using the inventive valving may be manufactured by this same sequential application of materials.

At the time of perforation of the material layer, fluid may be present adjacent to or in contact with the material layer above, below, or on both sides. In that case, energy deposited by or generated during the perforation process may be transferred to the fluid. Except for very rare configurations, the energy transfer is negligible compared to the heat capacity of the fluid. It is contemplated within the scope of the invention that a valve can be opened with an optical energy of less than 16 µJ. If all energy that goes into the base ablation were absorbed by one microlitre of water, its temperature would increase by about 0.002 degrees Celsius only.

According to the invention, by changing the time duration of the pulse or the focusing properties of the pickup, the valve diameter can be modified, and this feature can be effectively used in applications where fluid flow regulation is necessary, for example in mixture control, or where fluidic motion resistance (including its mixing) is affected differently by valves of different size.

It is contemplated within the scope of the invention that for microfluidic configurations and applications where sample or fluids are adversely impacted by thermal changes, heat sinks or cooling faces of heat pumps may be incorporated into the microfluidic network to compensate for any such thermal changes.

Multiplexing Operations

In one aspect of the present invention, the arbitrary position of the valve is exploited to implement logic for the flow of fluids. This can be implemented at any moment during the process as performed in the microfluidic apparatus, a feature referred to as real-time capability. Of particular interest is the logic scheme depending on the outcome of a previous operation. A microfluidic component that can perform this operation in the most generic way is hereafter denominated a multiplexer, analogous to the component in digital. electronics with equivalent functionality.

Figure 3A:
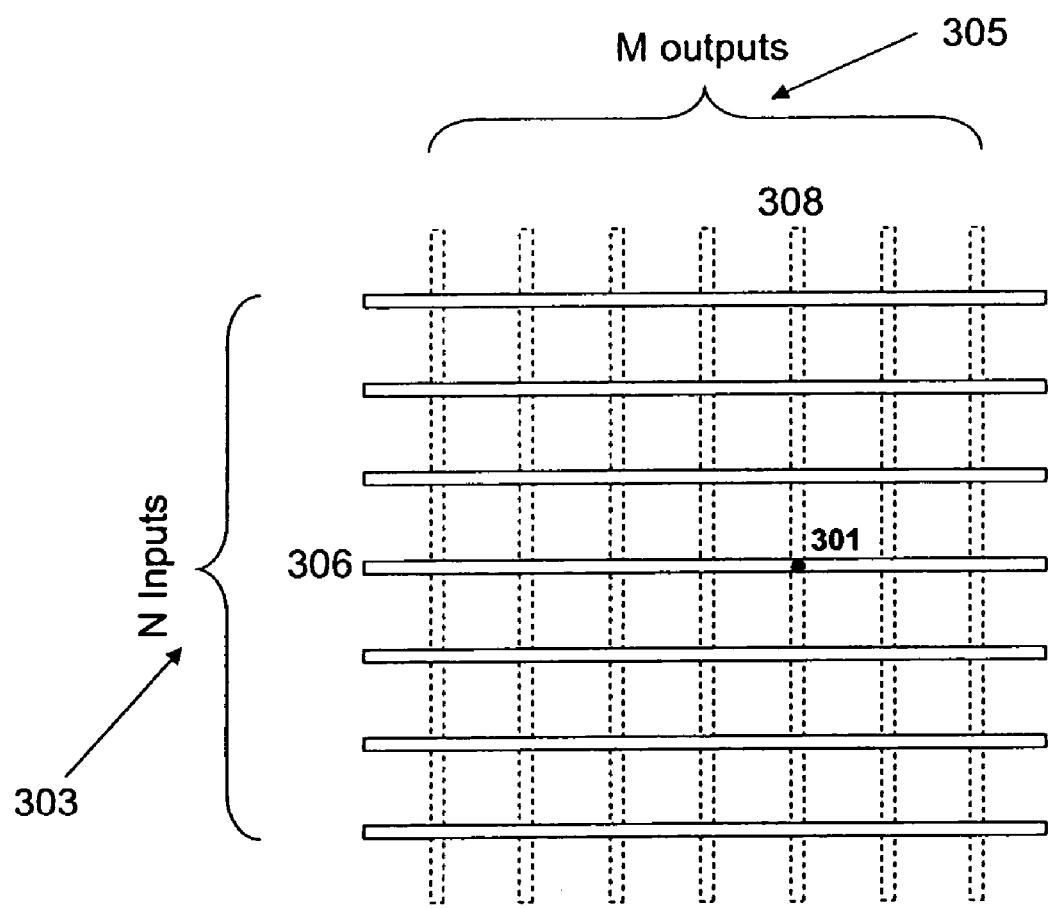
FIG. 3A illustrates a geometrical layout of the multiplexing nature of the inventive valve.

FIG. 3A illustrates one embodiment of the multiplexer, which includes a matrix of N input capillaries 303 on one side of the disk facing M output capillaries 305 on the other side of the disk. In the following, two fluidic components are considered to be facing one another when they are separated by the base only, in at least one position. The multiplexer therefore allows one or more of a set of inputs to be in fluid communication with one or more of a set of outputs. A set of capillaries is to be understood as two or more capillaries.

The simplest case is shown in FIG. 3A, where the opening of a valve in a first position 301 connects a first input capillary 306 with a first output capillary 308. After fluid communication has been enabled, the actual passage of fluid from the input capillary 306 to the output capillary 308 may be achieved by applying a force on the fluid. Examples of such force include spinning a centripetal device, exerting an overpressure in the input capillary line 306, or exerting an underpressure in the output capillary line 308. A proper venting design (not shown in the figure) ensures adequate escape for air contained in the fluidic components downstream from the moving fluid.

The extension of multiplexing to higher levels of complexity may be achieved using a multiplicity of valves at the crossing points in the matrix of facing capillaries. The valves enable fluid communication between the desired input and output capillaries.

Except to provide connections between a number of inputs to a number of outputs, the multiplexer may equally well be used to connect a number of inputs to a single output or a single input to a number of outputs. Since such connections do not by itself guarantee homogenous mixing in the first case or uniform distribution in the second case, the possible limitation may be somewhat mitigated by adjusting the time at which the different valves involved are operated, by preceding the multiplexing stage by appropriate volumetric quantitation, or by introducing intermediate multiplexing networks.

The multiplexer is primarily intended for use in a programmable device (such as the one described in the present invention) and to be an interconnecting network between different components of a microfluidic device. If a large number of input channels are to be connected to a large number of output channels, though not in all possible combinations, the physical size of the multiplexing network may be reduced by breaking it down in different stages with relatively lower integration.

Figure 3B:
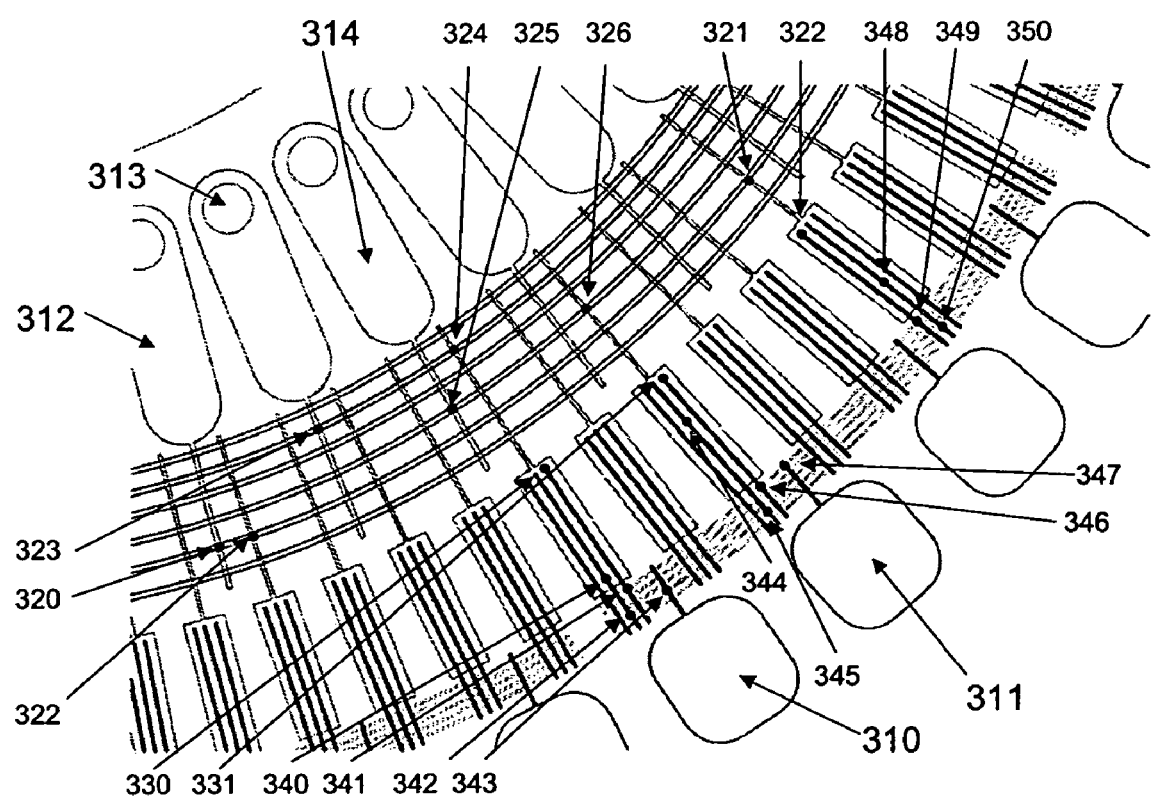
FIG. 3B illustrates the combined use of multiplexing units and dosimeters in an embodiment where three different fluids are dosed and collected into different reactors. This illustrative embodiment graphically describes the process control of an enzymatic assay where the inhibition of a drug compound on the enzyme activity on a specific substrate is tested in an homogeneous way.

In an illustrative embodiment, the combined functionality of the dosimeter and of the multiplexer is shown with reference to FIG. 3B. In this embodiment, a disk according to the invention is equipped with input wells 312,313,314. The input wells 312, 313, 314 are in fluid communication with a multiplexing matrix layer 316. The multiplexing matrix layer 316 is comprised of a grid of fluidic channels that are fluidly connected to dosimeter units 317 (here schematically represented as all having the same dimensions). The dosimeter units 317 are in fluid communication with segmented (separated) multiplexing units 318 that are in fluid communication with reactor chambers 310, 311.

In this scheme, for clarity of explanation, the venting lines are not drawn, even if they are an essential requirement in order to allow the fluid moving into a component filled with gas (air or any other inert gas sealed in the device at manufacturing).

This illustrative embodiment represents a generic microfluidic layout to perform a homogeneous assay. This assay can be used for the measurement of compound inhibition in an enzymatic reaction on a substrate, where the reaction kinetics (inhibition) is measured in real-time, by detecting the fluorescence emission polarization of convenient dyes. It is contemplated within the scope of the invention that many other assays known in the art may be used without substantial modification to the device configuration.

With continuing reference to FIG. 3B, an enzyme is pipetted into the input well 314, a substrate is pipetted into the input well 313 and a compound of interest is inserted into the input well 312. Knowledge of the pipetted amount is not required, and the choice of the input wells is totally arbitrary. The opening of valve 320 and valve 321 according to the invention allows the distribution the compound of interests into one dosimeter arbitrarily chosen. At the same time, more dosimeters can be used in order to perform parallel operation, and for example the compound is also diverted by opening valve 322 into another dosimeter connected to a different multiplexing segment in layer 317. With a similar operation, the appropriate substrate contained in the input well 313 is diverted into another dosimeter by opening valves 323 and 324, and the enzyme from input well 314 is taken to the dosimeter layer by opening valves 325 and 326.

The correspondence between input wells and dosimeters is defined by the user in real time, and allows matching in optimal way the dosimeter to the reagents according to the amount of fluid expected to be quantitated and the dosimeter volume.

The purging of the dosimeters occurs by directing into a waste reservoir the filled dosimeters opening valves 322, 330, 331 on the dosimeter layer, valves 341, 346, 349 on the segmented multiplexing layer, and valve 347 that determines the reactor 311 to be the waste reactor where fluids are consequently collected. It is contemplated within the scope of the invention that the inventive microfluidic disk can be configured so that no fluid exits from the microfluidic structure.

The actual assay is performed by dispensing the required amount of substrate in reactor 310, the amount being determined by the choice of the position of valve 340 and the choice of the reactor determined by the opening of valves 342 and 343. At any moment decided by the user, the compound and the enzyme can be added to the same reactor by opening, with the same logic, 348 and 350, 344 and 345.

It is evident that—by opening other valves—another reactor in the reactor layer could be filled by different amounts of the same reagents, or the reagents (for example the compound or the substrate) could be replaced by others stored in the input wells to have different reactions tested and measured. Even the reaction protocol (order of dispensing for example) could be different for different reactors.

Despite the apparent complexity, all operations have been reduced to a single process, which is the opening of a valve on the material layer at a desired location.

The procedure is independent of the type of fluids involved, and is constantly in control of the user at any time during the process. For example, the addition of a stopping agent after the reaction has started could be decided according to the data from the fluorescent readout.

Volumetric Quantitation

In another aspect of the present invention, an arbitrary position of the valve is exploited to perform volumetric quantitation of liquids in centripetal microfluidic components. The corresponding fluidic component will hereafter be referred to as a dosimeter 400.

Figure 4:
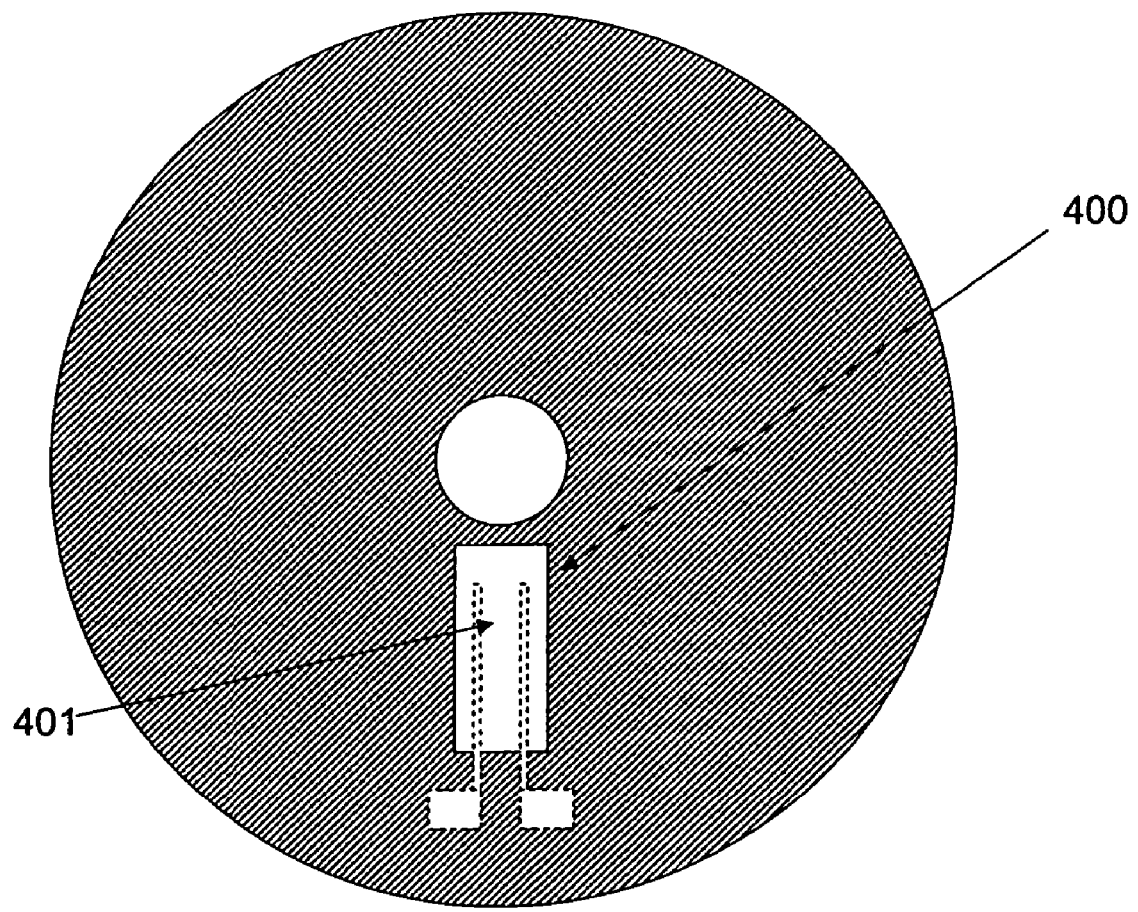
FIG. 4 illustrates a half section of the inventive disk containing the self metering embodiment according to the invention.

FIG. 4 depicts an illustrative embodiment for the dosimeter 400. It consists of an elongated reservoir 401 with the longest axis substantially positioned in the radial direction of the centripetal device. Along this axis, a portion of the device closer to the rotation axis will be referred to as upper, and the portion further from the centre of rotation will be referred to as lower. The shape and volume of the dosimeter are designed according to an amount of fluid to be quantitated and a desired resolution in the quantitation process. According to the invention, fluid is filled into the reservoir 401 through an inlet in the upper part (not shown), and a venting line 402 is present to allow the fluid to enter.

Figure 5A:
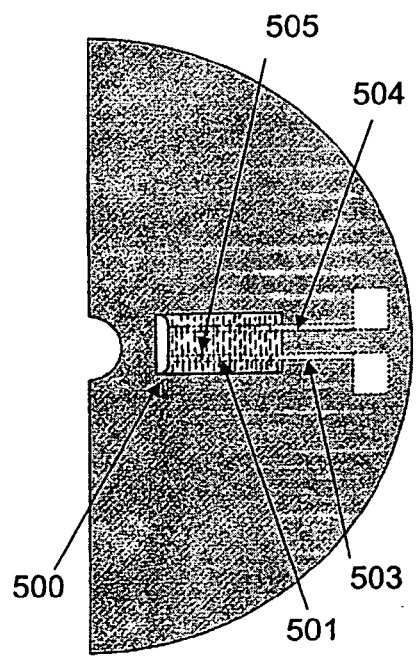
FIG. 5A illustrates the self metering embodiment according to the invention wherein a sample to be metered is within the sample metering chamber.
Figure 5B:
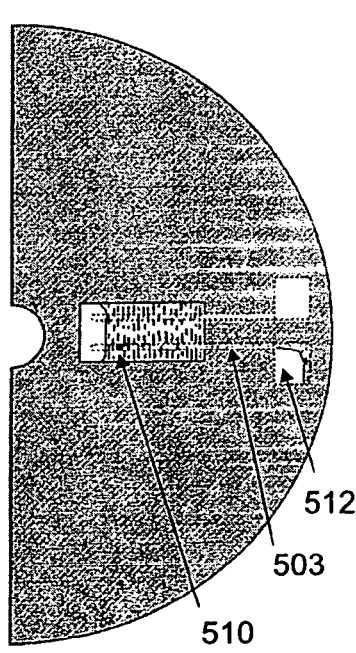
FIG. 5B illustrates the self metering embodiment according to the invention wherein a sample to be metered within the sample metering chamber is valved in a manner allowing the fluid to exit.

Turning to FIG. 5A to 5G, when the device is rotated, the centripetal force causes the fluid to move into the lower part of the reservoir 501 as shown in FIG. 5A. The capillaries indicated as 503 and 504 constitute two different outputs of the dosimeter 500. One of the capillary outputs, 503 in the specific case, is used as a purge line. Output lines are situated in the side opposite to the side containing the dosimeter, separated from it only by the material layer. The overall number of output lines depends on the specific application or implementation.

Figure 5C:
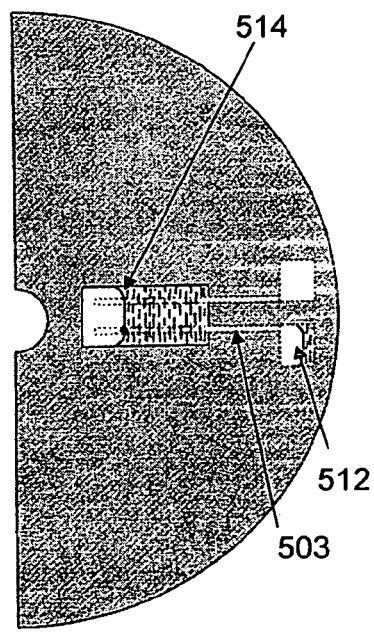

The first operation of the quantitation process consists in evacuating part of a liquid 505 to be metered into the purge line 503. This evacuation is achieved by opening a valve 510 by perforating the material layer in first position 510, and spinning the centripetal device to achieve this result. Any liquid 505 above the level defined by the valve 510, as a consequence of the applied centripetal force, flows into the purge line 503 and eventually into a first purging chamber 512. The liquid 505 remaining within the reservoir 501 forms a meniscus 514 as depicted in FIG. 5C.

The extraction of a defined volume of liquid 505 from the reservoir 501 may be performed by creating a second valve 515 in correspondence of the second capillary 504 line that puts into fluid communication the reservoir 501 with the second capillary line 504. The liquid contained in the dosimeter between the first valve 510 and a second valve 515 is extracted in the second capillary line 504 by spinning the centripetal device and applying centripetal force. The position of the valve in relation to the meniscus 514 within the reservoir 501 and the knowledge of the reservoir's 501 geometrical shape, allows the determination of the volume of liquid extracted into second capillary line 504 which flows into a second metered chamber 516.

As highlighted in position 514 of the figure, liquids in meso-scale fluidic components generally display a significant meniscus 514, i.e. the upper level of the liquid will not typically be flat. This behaviour varies among liquids and depends on surface tension, hydrophilicity and hydrophobicity of materials, thus making the shape of the meniscus unpredictable. It is a benefit of the present invention that the volumetric quantitation is substantially independent of knowledge concerning the meniscus shape. The same liquid, in the same geometrical conditions and in contact with the same materials, will exhibit the same meniscus shape, rendering the quantitation process independent of the meniscus shape.

A single dosimeter may be used for various liquid extractions on the same output line. FIG. 5F shows how opening an additional valve, in third position 520, allows the extraction of a second volume of liquid into the next step of the microfluidic network. The second metered amount is sent to the metered chamber 516 as shown in FIG. 5G. This is called the multi-spill capability of the dosimeter.

Another aspect of the present invention is the multi-output capability of a single dosimeter. The same dosimeter may serve various output lines, so that the same liquid may be sent to an output by opening a valve in an appropriate position connecting the dosimeter to the mentioned output line.

Quantitation may occur in real-time at the same time as fluid processing. For example, the multi-output capability of the dosimeter may be used to keep the pH of a reaction constant, by subsequent extraction of an acid or of a base, according to feedback provided by the reaction itself while the reaction occurs.

Another application of the dosimeter is in the phase separation of fluids by means of centrifugation. For example, blood can be separated into its components (plasma, lymphocytes and erythrocytes) by means of centrifugation and possibly additional reagents (sucrose or Ficoll by Amersham for example) inside a dosimeter. The opening of valves near or at the separation interfaces allows the separation into different outputs of the dosimeter of the various components, in an adaptive way. Similar separation can be performed on fluids containing cells or lysates, on emulsions or on suspensions of particles.

The capability of dispensing amounts of fluids when desired by the user has also an active role in mixing. For example, the dissolution of a solid phase chemical entity into a solvent depends on its concentration in the liquid phase. It is possible to dispense an amount of fluid into a "siphon" shaped capillary where the exceeding liquid exits from a position located at an inner radius. The amount of liquid can be left in contact with the solid phase solute for an amount of time sufficient to allow diffusion to occur. Then, by means of the valve, an additional amount of fluid can displace the previous solvent, remaining in place for additional dissolution of the solid phase but with a reduced initial solute concentration. This operation can be repeated various times for repetitive dilution of the solid phase chemical entity.

Redirection in a Centripetal Device

A common problem in centripetal devices, especially if complex processes are implemented, is related to the unidirectionality of the centripetal force. Given a fixed rotation axis, the fluids move only from inner to outer positions, and the process terminates when the position of the fluid reaches the outer edge of the centripetal device. This feature excludes the use of centripetal devices in cases where the process to be accomplished comprises a large number of steps. Here, as in the following, the "radial position of a mass of liquid" denotes the radial position of the centre of mass of the liquid.

In one aspect of the present invention, the above limitation is overcome by an appropriate arrangement of the inventive valves within a microfluidic circuit. The process of moving a sample liquid from an outer to an inner radial position by means of the centripetal force itself is referred to as reflow. The required energy is obtained at the expense of the potential energy of another mass of fluid, hereafter called buffer fluid, whose only purpose is to provide energy for the reflow process. The mass of buffer fluid can be placed at any radius on the disk, and the buffer fluid can have any density. Overall energy conservation constraints link the characteristics of buffer and sample liquids, specifically the respective volume, density, initial radial position, and final radial position of buffer and sample liquids. Another possibility for reflow consists in making use of additional sources of energy like differences of pneumatic pressure or chemical energy. In a way similar to the one described in the next section "fluid transport activated by a valve", a bottle could be actuated in order to push or pull the liquid towards an inner part of the disk. The pneumatic overpressure or underpressure, for example, could be generated by the centripetal force itself by having a mass of liquid compressing or decompressing a gas volume. In this case, the energy could be stored by avoid the fluid to move back when the centripetal force is reduced, for example by having a Tesla valve or similar functional device onto the path of the liquid. The stored energy can then be recollected in a later moment when the centripetal acceleration has been reduced, and used to reflow the sample fluid.

Figure 6:
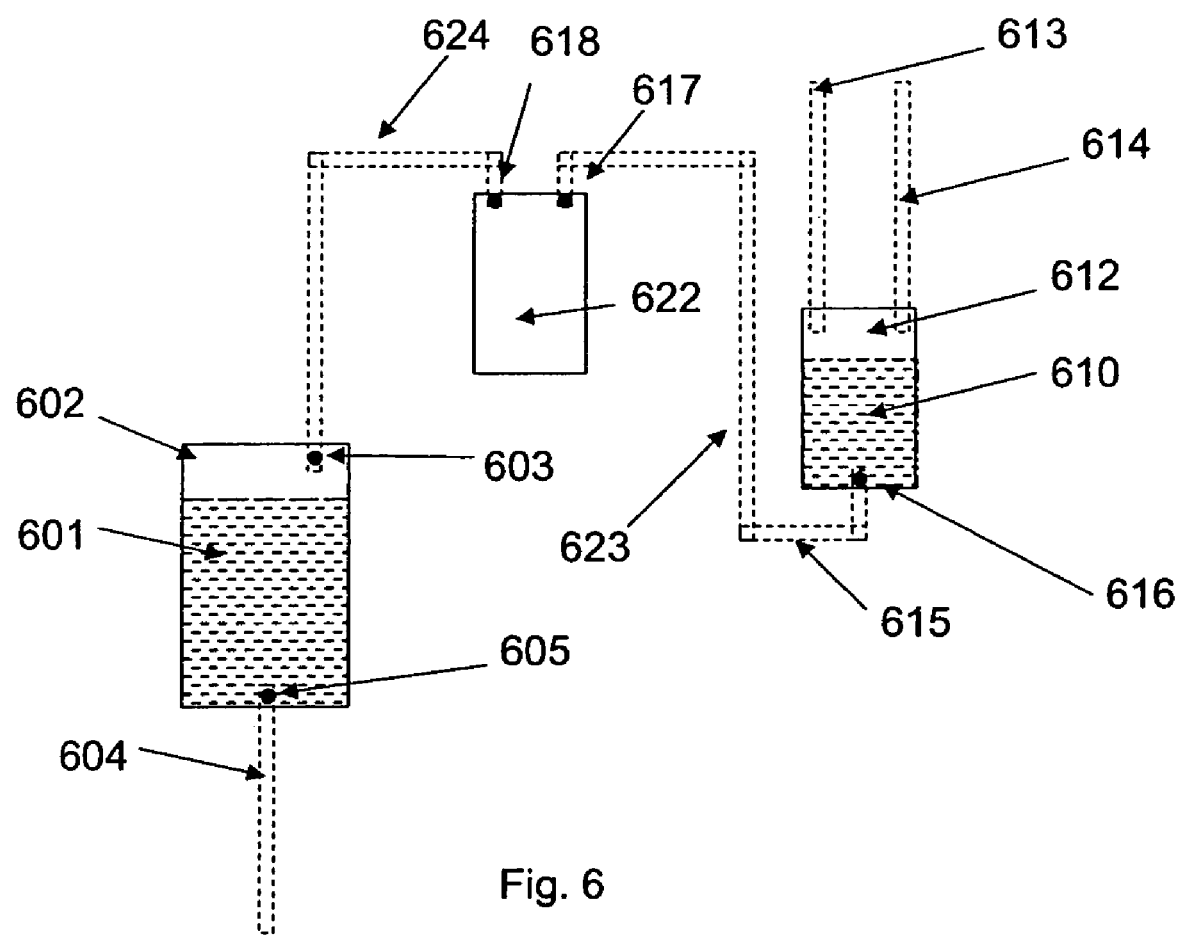
FIG. 6 is a schematic depiction of the reflow embodiment according to the invention.

An illustrative embodiment of the reflow method consists of the following steps, as illustrated in FIG. 6: The buffer fluid 601 is loaded in a reservoir 602. To the extent that the buffer fluid 601 does not participate in any reaction or process, the liquid used is independent of the use of the disk. Accordingly, buffer loading may be performed at the disk-manufacturing phase. An important requirement is for the reservoir 602 to be gas-tight, i.e. sealed to prevent air or gas to freely enter or exit. The sample liquid 610 flows into a sample reservoir 612 through position 613. For this operation, the sample reservoir 612 requires a venting line 614. In these conditions, the sample liquid 610 generally cannot flow through the capillary 615 since the presence of air—trapped below the liquid mass—impedes the flow of the liquid into it even if valve 616 would be already open.

The opening of a first valve 603 along the fluid communication circuit enables fluid communication between reservoirs 602 and 612 if valves 617 and 618 are already open Where appropriate, an additional reservoir 622 referred to as a trap, can serve to collect the sample liquid 610. When fluid communication is enabled, it does not by itself lead to a movement of the fluids, because the potential energy is at a local minimum, with the buffer fluid 601 prevented from flowing into a second capillary 604. The buffer fluid 601 and the sample fluid 610 are integral elements to guarantee the gas-tightness of the fluid communication circuit, and the reservoirs 602, 612 are designed to maintain this gas-tightness up to the end of the process. Opening a second valve in position 605 enables the reflow operation. The reflow operation is initiated by spinning the centripetal device, thereby exerting on buffer liquid 601 and sample liquid 610 a force proportional to their mass and to the acceleration $a=\omega^2*r$, where omega is the angular velocity of the device and r the radial position of the liquid, neglecting Coriolis forces.

The movement of the buffer fluid 601 into capillary 604 causes a reduction in the gas pressure in the fluid communication circuit. For appropriate kinematical conditions, this results in a suction force, pulling the sample liquid 610 from position 615 into the trap capillary 623, and moving the gas contained in the trap 622 into the reservoir 602 through a reservoir capillary 624. Suction is the process whereby a force is exerted upon a liquid body by reason of reduced gas pressure over a portion of its surface.

When the sample liquid 610 reaches the trap 622, the centripetal force causes it to move towards the bottom part of the trap 622. The suction of the reservoir capillary 624 is not exerted on the sample liquid 610, but on the gas above the liquid mass, so that the sample liquid 610 contained in the trap 622 does not enter into reservoir capillary 624.

When the entire sample liquid 610 has been sucked into the trap 622, the communication circuit is no longer gastight and atmospheric pressure, through the venting line 614 or through the input line 613, enters into reservoir 612, trap capillary 623, trap 622, reservoir capillary 624, and reservoir 602. At this moment, with the centripetal device still spinning, the buffer fluid moves completely into the exit capillary 604 and the final state of the reflow operation consists of the sample liquid 610 having moved from reservoir 612 to the trap reservoir 622.

The reflow operation allows longer processes to be performed in a given centripetal device. With the trap reservoir 622 at a smaller radial position than the sample reservoir 612, a long process may be broken down as follows: the first series of steps may be performed by moving liquids from an inner to an outer radial position, comparable to sample reservoir 612, reflow is then applied to bring the liquid to the trap reservoir 622, at which point the remainder of the process may be performed, moving again from an inner to an outer radial position. The number of reflow operations is generally limited only by the amount of buffer liquid that is loaded onto the disk and its radial position.

The relative radial positions of the sample reservoir 612 and buffer reservoir 602, and of the trap reservoir 622, are arbitrary. However, a given set of relative radial positions will determine the minimum mass of buffer liquid for a given mass of sample liquid. The choice of radial positions may be driven by the required configuration of input and output ports. For example, input ports may be distributed in a rectangular shape array covering the top side of the disk, and buffer liquid reservoirs may be used to reflow the input liquids into traps located at the minimal radial positions available on the disk. Typically, the minimal radius accessible corresponds to the circumference around the spindle support. The output of the process, generally available at maximal radial positions, may be transported with the same reflow procedure into an array uniformly distributed on the top surface of the device, including the same array used as input.

A functionality similar to reflow, that can be assimilated to reflow, consists in washing steps during a biological or chemical protocol. The washing procedure is performed by aspiration of the liquid contained in a reservoir of appropriate shape towards the inner part of the disk, so that the reservoir, after washing, can still be filled with other liquids that do not flow out. This procedure is particularly relevant for the execution of heterogeneous assays, and can be performed by a variant of the reflow method already explained. It is contemplated within the scope of the invention that the buffer fluid 601 can be either liquid or gas.

Positioning System of the Pickup

One aspect of the present invention concerns the setting and knowledge of the pickup position, at a given time, with respect to the disk reference frame. This position may be decomposed as a focussing position, a polar position and a radial position. These directions are the cylindrical coordinates of the pickup head in the reference frame of the rotating disk, with the rotation axis corresponding to the cylinder axis.

The focussing movement of the pickup head, relative to the base surface, has already been described and can be achieved by "voice coil" movement of the focussing optics or of one of the light sources or of any other optical element. Indeed, the focussing mechanism employed in standard compact disk drivers performs this operation, together with a fine-tuning movement of the lens in the radial direction.

Radial positioning of the pickup may be achieved by means of the previously mentioned voice coil, together with a coarse displacement of the pickup assembly. Different types of motors, including linear motors, DC motors, servomotors, and stepper motors, may achieve this displacement. Rotating the disk around its axis performs polar positioning at a given moment of the pickup.

One conventional solution includes using high-resolution optical encoders: a rotary encoder for the polar position and a linear encoder for the radial position. In addition, digitally encoded information in the radial and polar directions, stored onto the disk, may be used to determine where the spot is directed following art, each of which is incorporated by reference. Gordon (U.S. Pat. No. 6,327,031, U.S. 22085202A1) teaches an apparatus and method for carrying out analysis of samples; Virtanen (U.S. Pat. No. 6,030,581) teaches a laboratory in a disk; and Mian et al. (US2001/0055812A1) teaches devices and methods for using centripetal acceleration to drive fluid movement in a microfluidics system with on-board informatics.

In one illustrative embodiment of the present invention a method to determine the radial and polar position of the pickup head is provided. Specifically, in the reference frame of the disk, the radial and polar position are determined using timing information, as measured from the occurrence of a signal from the pickup induced by markers, of the rotating device. The pickup measures (as in commercial CD driver pickups) the light reflected from the scanned surface.

A marker generally is a line on the base with specific optical properties, with a polar position varying as a function of the radius. Examples of specific optical properties are higher or lower reflectivity compared to the area around the marker. The marker may also be situated on a side, and may include a capillary filled with a liquid with peculiar optical properties—defined as including reflectivity, absorption or fluorescent emission. The change in reflectivity may be detected and provides a signal whose time may be recorded. This is referred to as the time of a marker signal in the present invention.

If the rotational speed of the device is constant over at least one rotation period, the marker signal offers a precision measurement of the rotational period of the disk and therefore of its instantaneous rotational speed. The time elapsed from the occurrence of a marker signal divided by the rotation period, is in itself the measurement of the polar position of the pickup with respect to the disk. According to the invention, a solution for a simpler transformation into polar coordinates is therefore a marker which is a straight line, where all the points have fixed polar coordinates (polar angle equal to zero) and the previously mentioned ratio multiplied by two (2) times π indicates the polar angle position at a given moment.

The addition of a second marker allows the measurement of the radial position, provided the polar angle difference between the two is a non-constant function of the radial position. An example non-constant function is the following:

Polar coordinate=radial coordinate*Constant1+Constant2.

Other specific shapes, also non derivable and non-continuous or with zigzag shape, can be envisaged typically in order to occupy a limited angular sector of the disk, while keeping the necessary polar and radial coordinate resolution on the instantaneous pickup position. With knowledge of the rotation period and the time difference between the two markers a polar position of the second marker, with respect to the first one, may be determined. Given the shape of the two markers, the difference in polar position is then used to determine the radial position of the pickup in the disk reference frame.

According to the invention, the properties of the second marker differ from those of the first marker such that the two markers may be distinguished on the basis of the signal produced by the pickup. Suitable properties include reflectivity, width, structure, line duplication, and the like.

This method assumes that the disk rotates around a fixed and known axis, defining the origin for the radial and polar coordinates. In practical cases, a removable disk is subject to misalignments when mounted on a spindle support, and the actual rotation axis does not necessarily coincide with the expected one. Additional markers may be provided to determine the actual rotation axis of the disk to address this issue. More specifically, the measurement of the time difference between markers may be used to verify the assumed axis position. With more than two markers of known shape, the time difference between them contains information on the axis position. The axis position may be inferred by minimizing the difference between measured time differences and time differences expected on the basis of a given axis position.

This method may also be applied to devices that rotate around an axis lying outside the device's perimeter. In the case of rectangular shape disks, not only may the relative position of the pickup head with respect to the disk be determined, but also the disk position with respect to the rotation axis (including rotation) may be determined on the basis of a sufficient number of markers on the disk. The number of markers required depends on the accuracy needed.

Temperature Monitoring and Control

Due to the structure of the disk, its temperature may be controlled by application of an external heat or cooling source. The sides may have transparent or absorbing properties to thermal radiation and, in particular, to electromagnetic radiation in the infrared or microwave light spectrum. It is recognized that other heat exchange mechanisms other than radiation could be used, including convective fluid flow, resistive heating and conduction. For integrated microfluidic devices, it is often useful to have a means to determine the local temperature. In particular determining local temperature is useful for rapidly varying thermal cycles such as those required for the polymerase chain reaction (PCR).

The two-layer structure of the disk may also allow for two facing reservoirs: one used for the sample fluid whose temperature requires monitoring, and the second one containing a thermometric liquid. In a preferred embodiment, the thermometric liquid is based on water or alcohol. Because of the material layer thickness, there is generally a large thermal conductivity between the two fluid masses, so the temperature of the thermometric liquid may be approximated as the temperature of the sample liquid. The thermometric liquid temperature may be monitored as classical thermometers by measuring the (relative) expansion coefficient of the fluid, with respect to the volume it has at a reference temperature. Accordingly, the liquid contained in the capillary moves according to the volumetric expansion of the liquid inside the reservoir, and the determination of its position provides temperature monitoring.

Alternatively, the pickup light itself may be used for local heating of a fluid. By off-focusing the pickup light to irradiate a large area of the material layer, the material layer absorption—or the thermometric fluid absorption if the liquid is chosen accordingly—dissipates the energy as heat in the sample fluid, producing an increase of its temperature.

Furthermore, the pickup itself may be used to monitor the position of the thermometric fluid meniscus in a capillary, by evaluating the change of reflectivity corresponding to the air-liquid interface in the capillary. This evaluation may be performed by means of the focusing feedback mechanism described above.

Electrical Connections

According to the invention, the base may be used to distribute electrical connections to different parts and positions of the microfluidic circuit. Provided the base is an insulator, various techniques are available to deposit thin layers of conductive materials, including metals, conductive polymers, conductive inks and graphite. Some of the techniques (for example electroless chemical deposition of metals) also allow, through photolithographic techniques, to deposit the conductor in a specific shape and pattern, generating electrical distribution lines. These electrical lines may be used to generate electric fields, for example for electrophoresis, or to provide electrical power to components present on the disk. The electrical connections may be powered on the disk itself (micro batteries) or may exploit the presence of a magnetic field that, because of the disk rotation, induces an electric field on the conductor generating an electrical potential difference. The magnetic field, in particular, can be used to induce an apparent electric field onto a rotating disk, the magnetic field being used or for the generation of electrical currents or to generate an apparent electric field, for example required in protocols like patch clamp, voltage sensitive probe dyes and electrophoresis.

Alternatively, the conductors can have an electrical connection on the spindle support, typically by mechanical contact, which is subsequently connected to the fixed part of the apparatus by means of brush contacts, through conductors coaxial to the rotation axis or by conductive liquid connections.

Detection Devices

One aim of the present invention is to perform programmable, flexible and automated manipulation of fluids. In most applications, the detection of reaction products, meaning (in general) any detection of observable quantities consequent to a process, is of importance for a practical use of the device.

In the present apparatus, it is possible to use the pickup itself for various operations, by making use of the readout present in the device to perform the focussing onto the base. The reflectivity information of the materials present on the focal point of the pickup may be used not only for the scope of valves and disk operation, but also to produce data concerning the fluidic process.

In another illustrative embodiment of the invention, the reflected light may be associated with the position (in space)

of the pickup, to generate images by using the pickup as a con-focal microscope. Bi-dimensional images may be easily constructed by varying the radial position of the pickup during spinning, and collecting the data from the pickup, for example, by digitisation. Three-dimensional images (via the con-focal properties of the optics) may be constructed using the focusing movement of the pickup, and varying the distance of the pickup from the base. Due to the low depth of focus achievable by con-focal optical systems, three-dimensional images of the fluids (and of the objects contained in the fluid that have a size and optical properties which are detectable) may be collected and stored for analysis purposes. Counting methods, for example applied to cells present in the fluid, are possible and profit significantly from volume scanning to increase the statistical significance of the data present in a small volume sample.

In yet another embodiment of the present invention, the disk is essentially a flat, typically transparent, thin substrate containing fluids which may include additional devices. These additional devices may be used to collect information on the fluids contained in the disk. These devices could be biosensors, transducers or arrays of tissues, cells and molecules. Standard well plate reader scanners, for example, may collect information on the optical properties of the fluids contained in the disk in a vast range of the electromagnetic spectrum, with the aim of colorimetric analysis, fluorescence detection, and radioactive emission measurement.

In yet another embodiment, the disk can be used as an optical medium where the light is collected and transferred by internal reflection, possibly using prisms, lenses or other micro optical components integrated onto the surface.

Another possible readout technology relies on the loading, during the manufacturing process, of the sides or of the base material with scintillating dyes. A radioactive activity related to the assay is converted into light signals inside the scintillating material, and the light intensity is used as a measurement of the radioactivity of the sample. The same result can be obtained by loading liquid scintillator in a microfluidic component facing the sample, and separated by it only by the base.

It is contemplated within the scope of the invention that off-board detection may be utilized. Examples include mass spectrometers, irradiation with gamma, x-ray or neutron beams, and chromatography. Removable components within the microfluidic network, such as peel away MALDI targets foils or the like can be incorporated into the sides of the inventive disk. These peel away target surfaces can be advantageously positioned so that they form sides of chambers used for collection of a sample or samples of interest.

Mixing

In microfluidic devices, the fluid dynamics are typically dominated by laminar flow. In this sense, mixing—which is natural in the macroscopic world because of different phenomena like convection or turbulent motion—constitutes a critical issue. According to the invention, various mixing methods may be used. Magnetic beads may be transported in the fluids through capillaries, and can be agitated from the outside by the presence of a static magnetic field when the disk is spinning (or via a variable magnetic field). Another method makes use of material layer's elasticity; having the material layer facing a vibrating reservoir. The vibration may be achieved in different ways: mechanically or induced by external electric or magnetic fields.

Another method according to the invention makes use of variation of the angular speed and direction of the rotating disk, including the generation of vibrational and torsional modes at resonant rotation frequencies.

A further method consists in the use of the Coriolis force to generate turbulent flow inside the channels of the disk.

Alternatively, the fluid may be circulated, by changing the rotational speed of the disk, in alternated directions along the capillary. The reverse direction may be easily obtained by a pneumatic force generated from air (or gas) compressed into a reservoir that, when the rotational speed of the disk is reduced, returns the stored energy to the fluid.

Alternatively, simple diffusion can be very effective for appropriate geometry of the microfluidic components (for example, in capillaries).

The valve could also have an active role in mixing. Taking alternatively small amounts of two fluids to be mixed into the same reservoir or capillary increases the surface of the interface and therefore mixing by diffusion. Short plugs of multiple fluids could be alternated inside a capillary for the purpose of improved mixing efficiency by using the output of the dosimeters.

Fluid Transport Activated by a Valve

The valves of the present invention have the remarkable feature to withstand large differences of pressure and to be gas tight. Therefore it is conceivable to have a pneumatic overpressure or underpressure on one side, which is followed by a sudden gas flow when the valve is opened.

A pneumatic overpressure can be easily made by means of a closed reservoir containing a volatile liquid or alternatively, by a chemical reaction between one or more components releasing gas, for example carbon dioxide. In another embodiment, the pressure could be generated by means of the centripetal force, compressing a liquid mass over a confined gas volume. In the last case, it is possible to store the energy for a time longer than the duration of the centripetal force by having the fluid entering into a Tesla valve that limits the motion of the fluid backward when the centripetal force is released. Such a system is hereafter called bottle. The volatile liquid, for example water, can be heated by means of the laser light in order to produce—by radiative energy transfer—a given amount of vapour. The connection of the bottle to another circuit, by opening a valve, will generate a pressure transient in the second circuit. With a multiplexer connection, a bottle could be put in pneumatic connection with one among a number of circuits. Once a valve is opened, the bottle is exhausted.

The liquid in the second circuit can be connected to a calibrated capillary—called output nozzle—exiting from the surface of the chip. By opening the valve, the liquid is forced to flow through the nozzle, and calibrating the amount of vapour produced it is possible to avoid the "spraying" of the chemical. The outcome is a collimated liquid jet exiting from the surface of the chip.

The sample disk can be piled above another one, called receptor disk, which has an input nozzle in correspondence of the output nozzle of the sample disk. The input nozzle is a hole connected to a capillary and able to collect the liquid. As an alternative, another bottle on the receptor disk could be used to suck the liquid by Venturi effect into a capillary, or by having a vacuum bottle with an underpressure aspirating the liquid into the device. The same method could be used in order to transfer fluids to and from devices with a different shape and purpose, such as microtitre plates, microfluidic devices with different functionality, analytical instruments or any device meant to modify the fluid properties (for example the fluid temperature). It should be noted that the technique of storing energy by means of a valve, energy that can be released in a controlled and desired manner, could be used in order to generate transient fluid flows with the consequence of mixing.

EXAMPLES

The following examples are provided to illustrate the methods and products of the present invention with particular choices for the several components and particular values for the several variables described above. As described above, many variations on these particular examples are possible. These examples are merely illustrative and not limiting of the present invention.

Example 1

Figure 7:
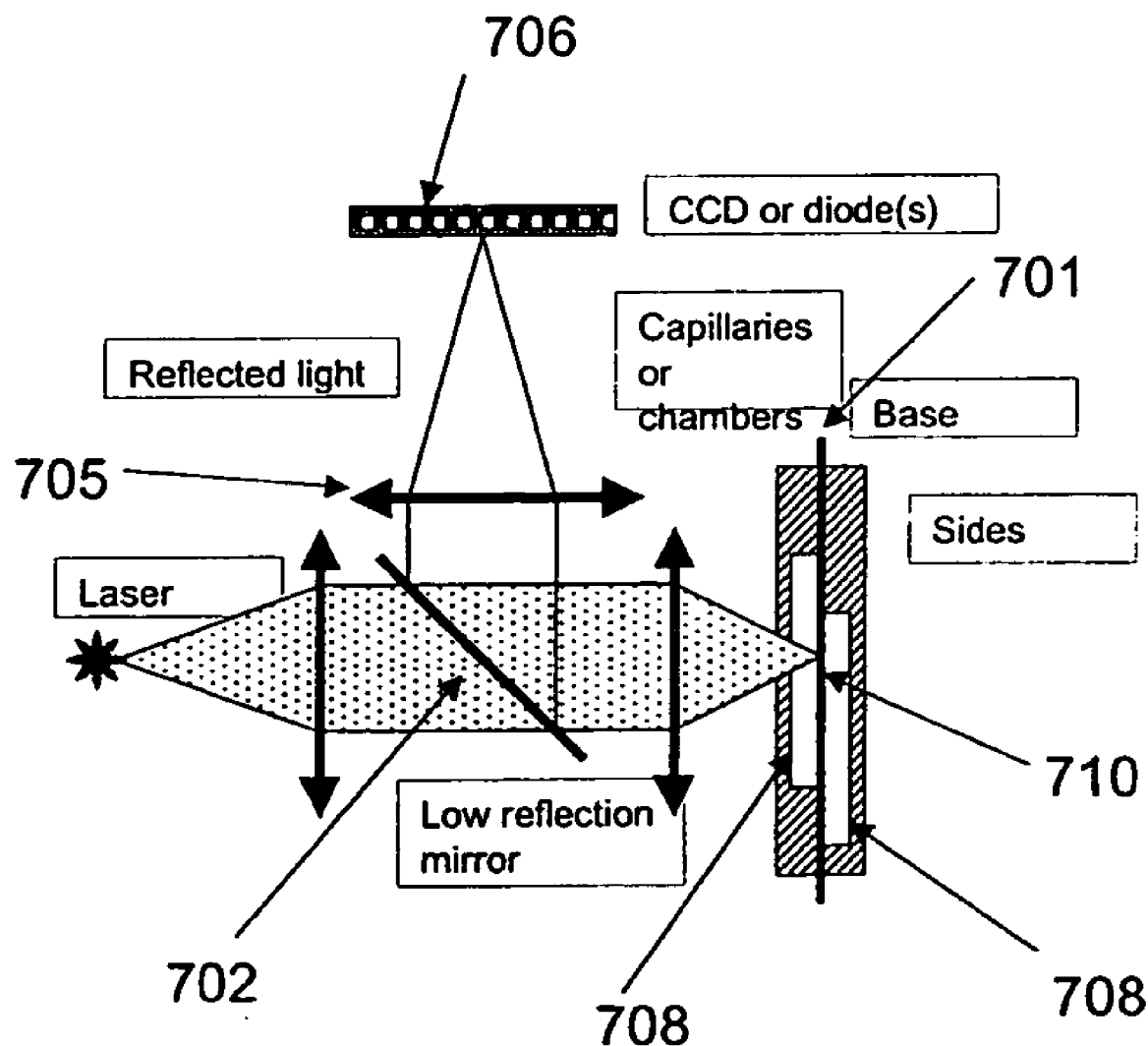
FIG. 7 is a schematic that illustrates the optical feedback according to the invention.

The optical feedback for focusing according to the present invention has been implemented to assess the correct positioning onto a material layer 701, as depicted in FIG. 7. Turning to FIG. 7, the optical feedback makes use of a simple glass 702 (about 0.199 mm thickness) that intercepts a few percent of the light reflected from the material layer 701 (through the same optical system used for the light incident onto the base). The light from the material layer 701 is imaged through a 48 mm focal length objective 705 onto a CCD 706. The CCD 706 records the actual shape of the laser spot onto the material layer 701, and can even image the material layer surface and—for example—beads floating in the fluid nearby the material layer.

It is contemplated within the scope of the invention that optical feedback can be achieved by the use of Astigmatic focusing. It is further contemplated within the scope of the invention that the laser junction image can be magnified or demagnified according to the ratio of the condenser focal length in the setup (currently 3.1 mm) and the CCD objective (48 mm). The CCD 706 also records images from the material layer 701 with a magnification of about 20×, a region of about 200×150 microns with a pixel resolution of 0.3 um. It is contemplated within the scope of the invention that the CCD 706 can be replaced with a diode (probably a matrix of 2×2 diodes to perform also astigmatic focusing with the same system) because essentially of a speed issue related to the focusing feedback (lock and tracking of the focus).

When working with a microfluidic platform such as a disk or chip, it is evident that three surfaces can be detected by this feedback method: the external surface of the side where the platform is in contact with atmosphere, the internal surface of the side 708 where the platform is in contact with the fluid (gas or liquid) contained in the capillaries (or reservoirs), an interface 710 between fluid and the material layer 701. This interface 710 is used and detected for focusing. It should be noted that—due to the very limited transparency (0.02% is the measured transmission for a material layer thickness of 10 micrometer and an Epolight 2057 dye concentration of 1% by weight in PMMA) of the material layer at the laser wavelength—whatever is behind the material layer 701 does not affect reflections of the laser light, but it is only detectable in transmission mode.

Working at low fluence, it was verified that the gradual base melting, and material layer 701 modifications, can be imaged by the same system, so to assess empirically the light density and temperature of the various parts of the elliptic spot.

Extending this concept, it was verified that it is possible and easy to detect if a valve according to the invention has been opened or not. When a laser spot was correctly focused, the entire region exposed to the laser radiation was ablated, and there was no material left, in focus, to reflect the light through the feedback optical system. If the material was not fully ablated, then the polymer forming the material layer 701 remaining in the optical path produced a reflection that was easily measured.

It was determined in real time if the inventive valve was correctly opened or if it had not been opened, and possibly repeating the opening step (for example, at the next turn of the disk) if necessary. It was found that the valve reproducibility, was better than ¹⁄₁₀₀₀, meaning that less than one over a thousand valves has possible problems in the fluid passage (verified by optical inspection). The optical feedback, allows for quality assurance of the operation of the inventive valve.

It was found that instead of fixing the energy of a shot, and perforating for a corresponding fixed time at a given power, it was possible to modulate the laser emission according to the feedback. The laser light was maintained up to the moment reflected light from the material layer disappeared, and then the laser was switched off. Advantageously, optical feedback allowed the laser irradiation to be reduced to a minimum, therefore reducing the amount of energy going into the system minimizing destruction or alteration of sample. Using optical feedback, the laser MTTF was improved significantly, as it is related to the temperature of the laser junction that increases significantly with the exposure time. Using optical feedback, it was possible to increase peak power of the laser, reducing the average shot pulse length. This allowed reducing even further the size of the heat transport region (whose diameter goes with the square root of the pulse time length); it also guaranteed that a valve had been correctly opened.

Example 2

Performance of the optical setup according to the invention can be characterized by the following example. The optical configuration is such, the energy of the beam after the CD lens and integrated all over its pupil amount to 16 µJ released in 10 µs, corresponding to 1.6W optical power. As expected, the original laser diode power of 6.2W was reduced because of collimation, matching and reflections in the optical setup.

When an 8 µm material layer of PMMA from Microchem loaded with Epolight 2057 was put on the CD lens focus, and a first shot was made, only approximately 7.6 µJ emerged from the base onto a pyrometer positioned behind the material layer. Neglecting reflections, which were expected to be about 4%, the remaining 8.4 microjoule were therefore deposited into the sample. As a reference, if the energy was uniformly deposited into a 1 microlitre water sample, its temperature would rise only approximately 0.0018 C. degrees. However, the energy was sufficient enough to fuse the polymer volume corresponding to the valve area (3 pL), computed at 7.5 µJ.

A second shot on the same position, showed that all the beam energy was measured on the pyrometer at the rear of the material layer. This measurement indicated that all the light was concentrated onto the valve surface and that increasing the shot duration did not release energy into the sample because the material layer was not absorbing it anymore since the light was passing through the base valve.

Figure 8:
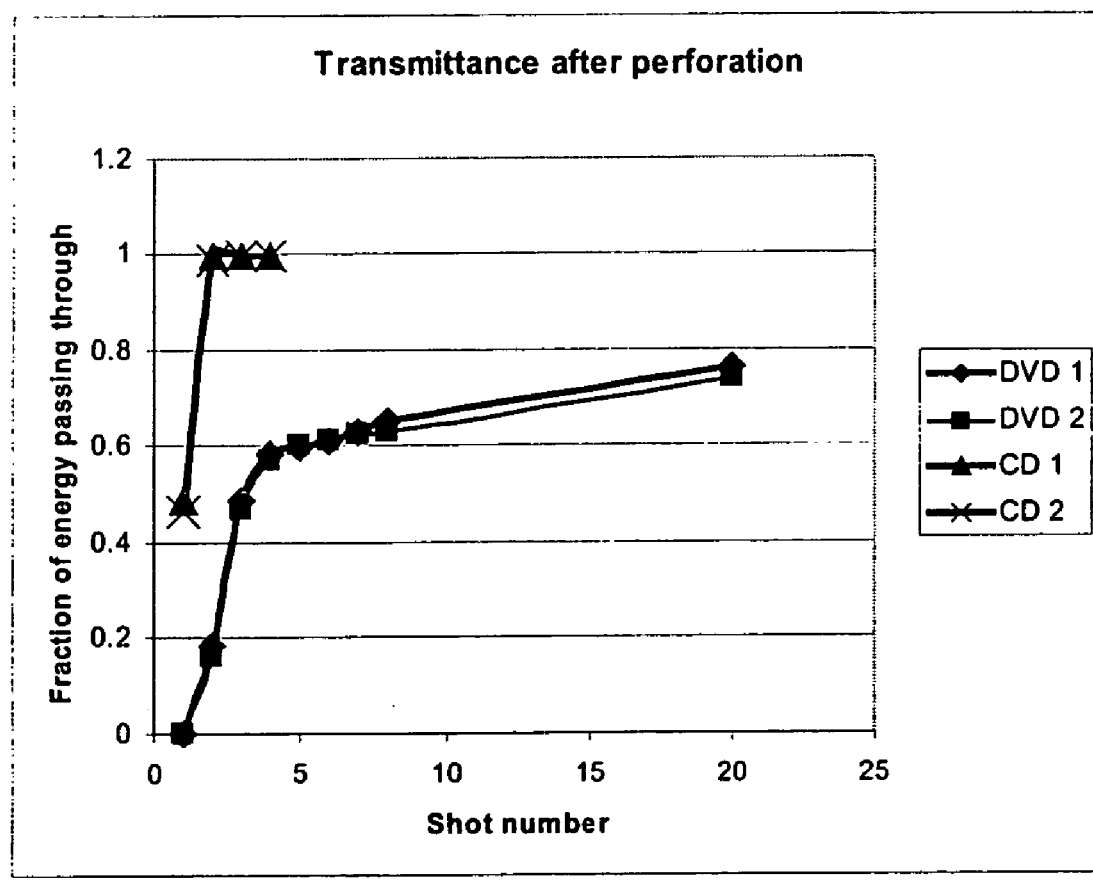
FIG. 8 is a graphic depiction of transmittance of energy passing through after perforation of the material layer.

As shown in FIG. 8 these above results are compared with data corresponding to a DVD configuration where a DVD optical pickup was used. In this case, the optical configuration was not optimized and, because of misalignments, aberrations and coma, part of the laser energy was not collimated onto the material layer in a concentrated spot. In this case, the full beam energy was not restored since it was still hitting the material layer that did not vaporize at low energy density.

Example 3

Performance of the laser according to the invention can be further understood with reference to the following example. The source of Laser emission used was the OSRAM SPL PL90_3 diode, having nanostack technology. The nanostack technology consists in the "vertical" or epitaxial integration of a number of discrete emitters on a semiconductor chip, and this produces a two to three times increase in maximum power. The specific diode exhibits an aperture of 20×10 microns, from three overlapping emitters that reach an optical output of approximately 75 W when limited to 100 ns pulse-lengths. The diodes were pulsed by means of a DEI PCX 7410 diode laser driver, from Directed Energy Inc. capable of covering the regime 20 ns to 1 µs at 10A, and 5A in CW mode. To access the regime above 10A, a DEI PCO 7120 hybrid OEM driver was employed. The pulse voltage and current was monitored by a Tektronix TDS2014 to reconstruct the electrical power onto the diode, and extrapolate its optical output on the basis of the diode specifications.

Both the condenser and the objective can be chosen among aspheric lenses (as those used in optical disks systems) and glass multiplets optimized to operate in the near infrared region (700–1100 nm). The incident beam was monitored by means of a Melles Griot (MG) wincamD CCD triggered by the laser diode driver, which intercepts the beam by means of a semi-reflective window. The beam was collimated into the objective and tuned by means of various Logitech QC 4000 Pro CCDs, which monitored the beam spot size onto the objective lens, the impact point onto the sample and the light reflected backward from the sample.

Figure 9:
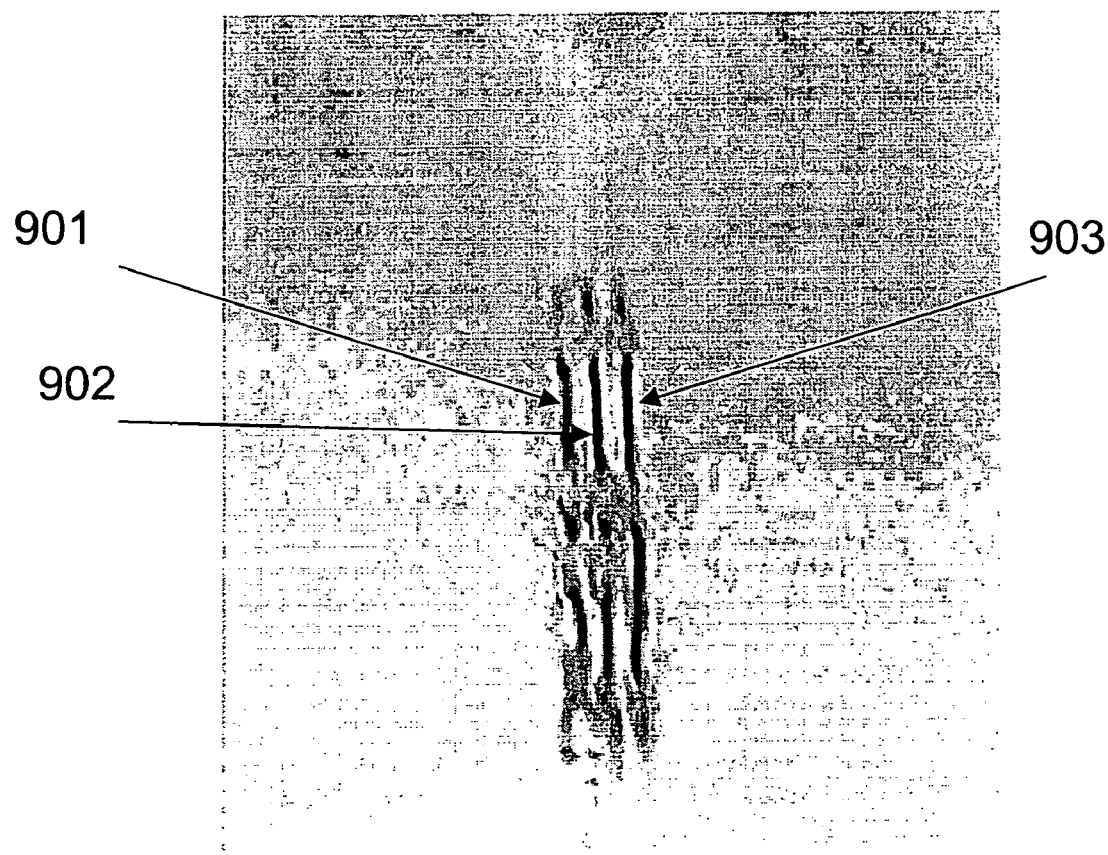
FIG. 9 depicts the nanostack structure of the laser diode upon a sample object.

In a preferred configuration, the objective is a CD lens with its voice-coil actuator that can be moved along two axes by means of current control. This configuration allowed optimizing optical conditions and permitted shot by shot verification that the laser beam is in optimal configuration and also permitted prints of the laser diode emitter showing the nanostack structure onto the sample as shown in FIG. 9. The nanostack structure is visible as three overlaid narrow slits 901, 902 and 903, which correspond to the three emitting junctions of the PL90-3 laser diode used in the experiment. The sample under test was a polyethylene (PE) film from a commercial disposal bag having a thickness of approximately 20 µm. The film was characterized by a high loading of carbon-black. The sample was exposed with a 6.5 mm objective (NA=0.615) MG 06GLC001 and a 25.6 mm condenser (NA=0. 156) MG 06GLC004 showing evidence of base perforation. The diode laser parameters were I=10A with a pulse-length of 100 microseconds, the focusing was performed by observing diffraction rings in the forward direction without direct observation of the laser spot on the base. The estimated optical energy of the pulse was below 3 µJ, which is an upper limit that depends on the diode temperature and power degradation that is expected to occur for this diode in this particular pulse-length regime. It was found that most of the light was detected behind the base and was not absorbed by the sample material.

Figure 10:
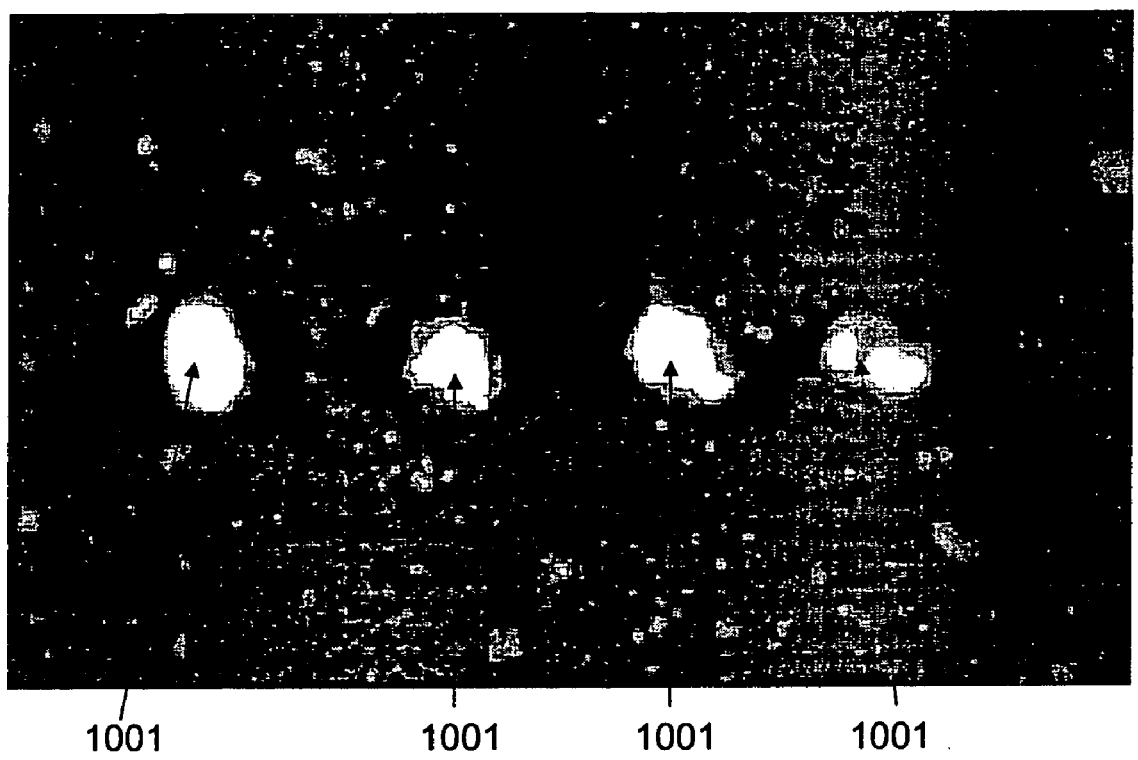
FIG. 10 depicts perforation entrance holes of a laser beam shot upon a sample object.
Figure 11:
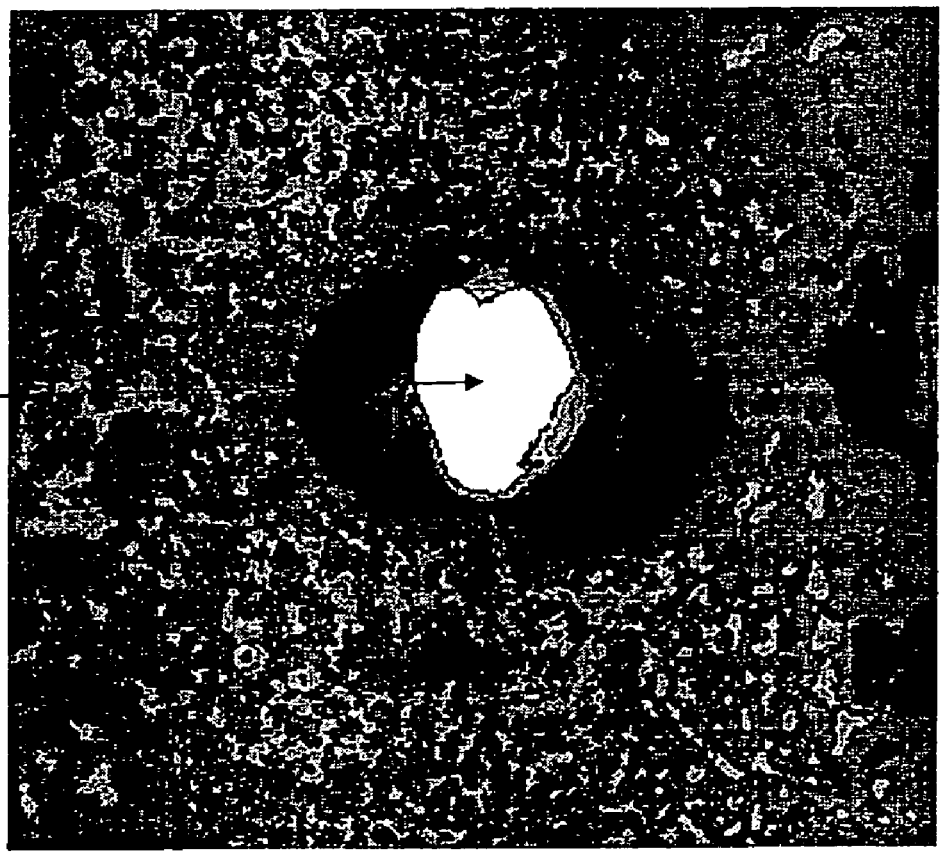
FIG. 11 depicts perforation exit holes of a laser beam shot upon a sample object.

The perforation entrance holes 1001 are depicted in FIG. 10. The perforation exit holes 1101 in FIG. 11. The pitch between the entrance and exit holes is approximately 174 microns allowing for an estimation of about 52 microns for the minor axis and 57 microns for the major axis on average.

Example 4

A solution of PMMA from Microchem of having a molecular weight of approximately 950,000 Dalton was dissolved at 11% in anisole and spin-coated onto a silicon substrate treated for detachment of the resulting film. The film was dried at about 20 degrees for approximately 24 hours. The spin coating technique resulted in a film having thickness homogeneity of approximately 1 micron over a 4 inch wafer. The surface roughness, measured by alphastep, was approximately 39.6 nm average roughness value and approximately 53.8 nm root mean square roughness. These mechanical properties of to the laser emission did not lead to any observable effects.

Figure 12:
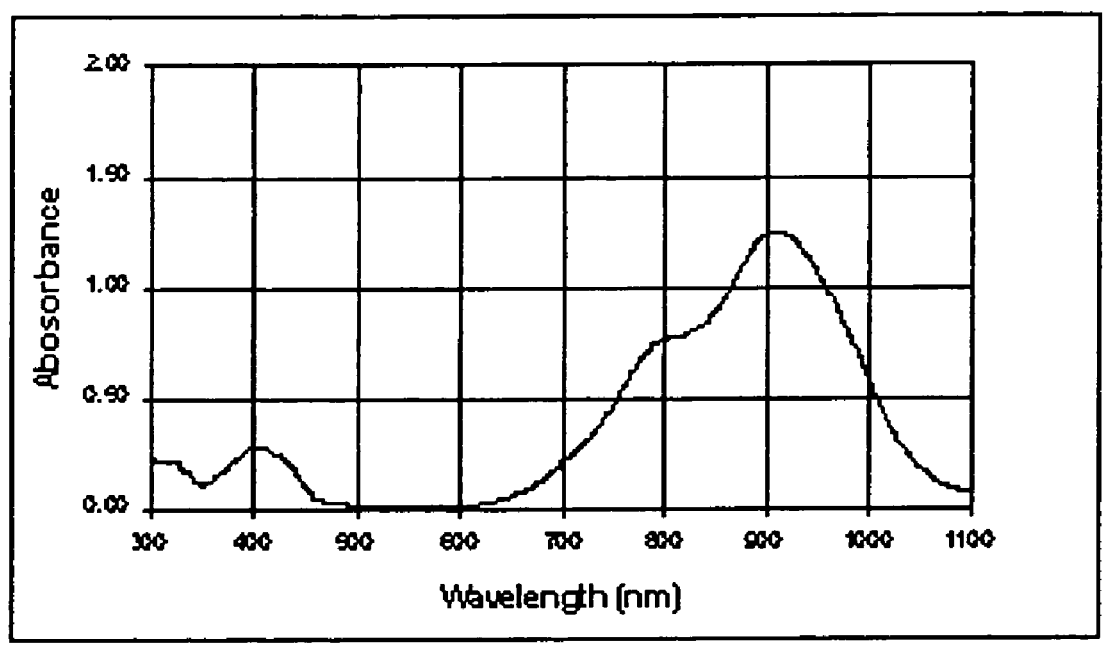
FIG. 12 is a graphic depiction of the wavelength absorption spectrum of an infrared dye incorporated into the perforation layer.
Figure 13:
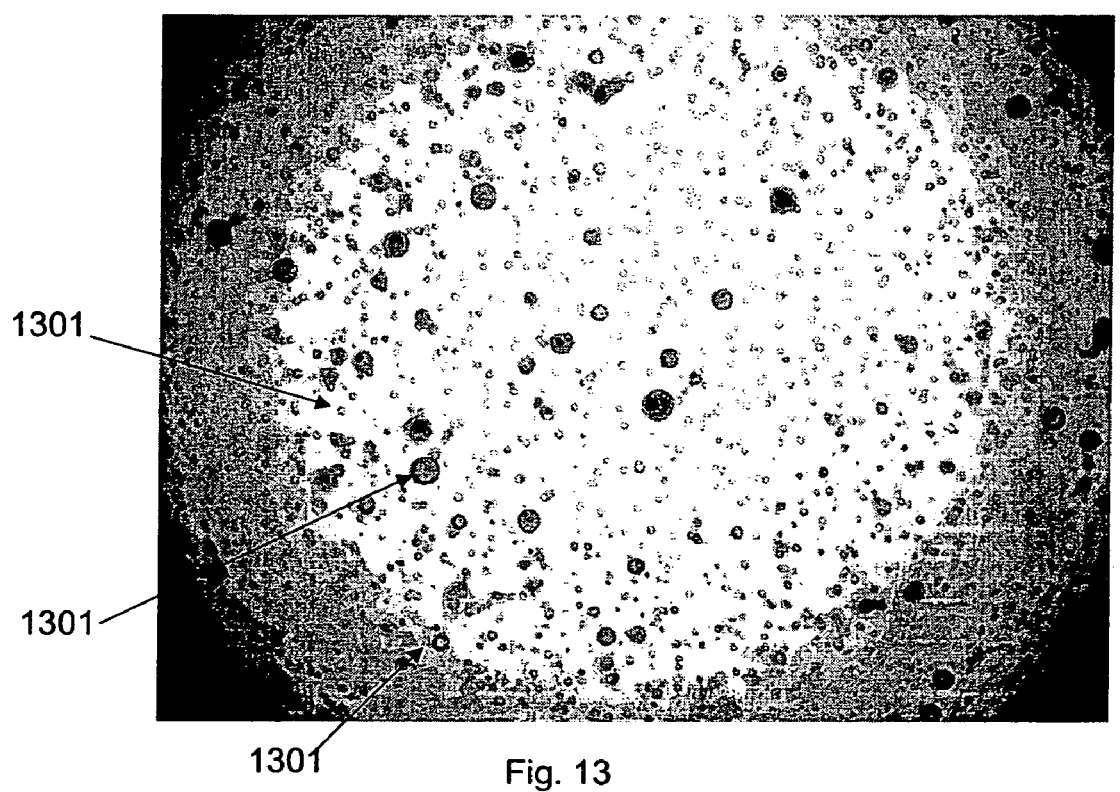
FIG. 13 depicts the distribution of an infrared dye within the material layer.

A further PMMA film was produced with a loading of approximately 0.5% by weight of ADS905AM, an infrared dye for American Dye Source Inc., whose absorption spectrum is shown in FIG. 12. The film was optically perfect to visual inspection but a microscopic analysis revealed that the dye was not uniformly dissolved into the PMMA. Upon microscopic analysis it was found that the dye was in sort of an "emulsion" form or dispersed as non-uniform globules 1301 as depicted in FIG. 13. Despite this lack of uniformity, no observable laser light was transmitted through the dye loaded film.

Upon exposure to a single laser shot of 100 ns, at 40A, the dye loaded film produced energy loss into the dye globules. While the non-uniform globules 1301 at the surface often exploded, no penetration at this exposure occurred.

Upon exposure to multiple laser shots, having a configuration as set forth in example 3, at a frequency of 1 KHz, visible penetration was observed. Such penetration did not achieve the sample depth of 20 microns; however, the laser light starts to be transmitted through the polymer foil. This transmission possibly indicates degradation of the dye absorption in the irradiated region. Without being bound by any particular theory, this effect is thought to be due to heat generation and subsequent thermal degradation of the dye molecule ($C_{62}H_{96}N_6SbF_6$).

It was found that single laser shots of 10 µs duration and 10A current produce openings that are passing through only when accurately focused. The laser setup used to produce the laser shots as within this example made use of a commercial CD pickup objective that required manual focusing at small power and exploited a laboratory grade 25.6 mm condenser as used in the laser setup. The hole diameter was about 20–25 microns (minor axis) by about 30 microns (major axis). The hole configuration exhibited memory of the laser aperture shape on the entrance side. This memory of the laser shape is neither a problem nor limitation. It was found that when the laser focusing was not perfect, the holes are often not passing-through. It was also found that by increasing the laser shots to 20 microseconds would be enough to effectuate a passing through. It was concluded that a 10 µs laser shot at 10A is sufficient for perforation in these conditions provided the laser is correctly focused, the optical dye is evenly dispersed and the material layer is about 8 microns.

Example 5

The following experiments were designed in order to maximize the damage to different biological samples induced by the VLV (Virtual Laser Valve) opening. This was accomplished by the following strategy: Maximize the number of valves in a given volume of fluid; increase the laser shot energy to a value which is significantly higher than the one expected for the prototype/product; minimize the amount of biological sample used in the experiment which is not exposed/affected by the VLV damage; and having different means (redundancy, calibration samples, and statistical tests) to assess the correctness of the assumptions and to validate the experiment consistency.

The first objective implied a large VLV density, and the capability to open a large number of VLV in a short time (below 30 minutes). Matrices from 100 VLV/mm2 to 600 VLV/mm2 were produced, the last value corresponding to the condition where the base is destroyed (cut) by the laser within known parameters.

The Laser parameters were kept, during all the experiments, equal to 100 µs shot producing 160 µJ of optical energy, largely sufficient for perforation with good margins.

Fluorescent beads, mixed at a known concentration in the samples, were used for a quantitative check of the dilutions and sample recovery efficiency in most of the experiments.

The samples were exposed in two main configurations: inside an experimental chip and in the so-called "drop" configuration. In all cases, the material layer was identical in thickness and dye loading.

The data was presented in a unique manner: the calibration samples were averaged and renormalized to 1 (100%), independently for beads and the biological measurement on the calibration sample. Every result was expressed as the relative amount of material collected when the sample is exposed to the valves divided by the corresponding reference unexposed sample. The term "loss" corresponded to the relative difference (REF−VLV)/REF, which was a positive number in case of a biological loss or damage, and a negative number in case the exposed sample had more material than the reference sample.

Chip Experiments Description

With the exception of the pro-insulin exposures, one micrometer diameter YC carboxylated fluorescent beads (Polybeads from Polysciences, Warrington, Pa., USA) were added to sample in order to achieve, after final dilution, a concentration of 50 beads/µL. The beads were used also to verify in qualitative terms the sample inside the chip, and to monitor the chip rinsing by means of a fluorescent microscope. Calibration samples, as well as negative samples, were produced by standard dilution techniques.

Figure 14:
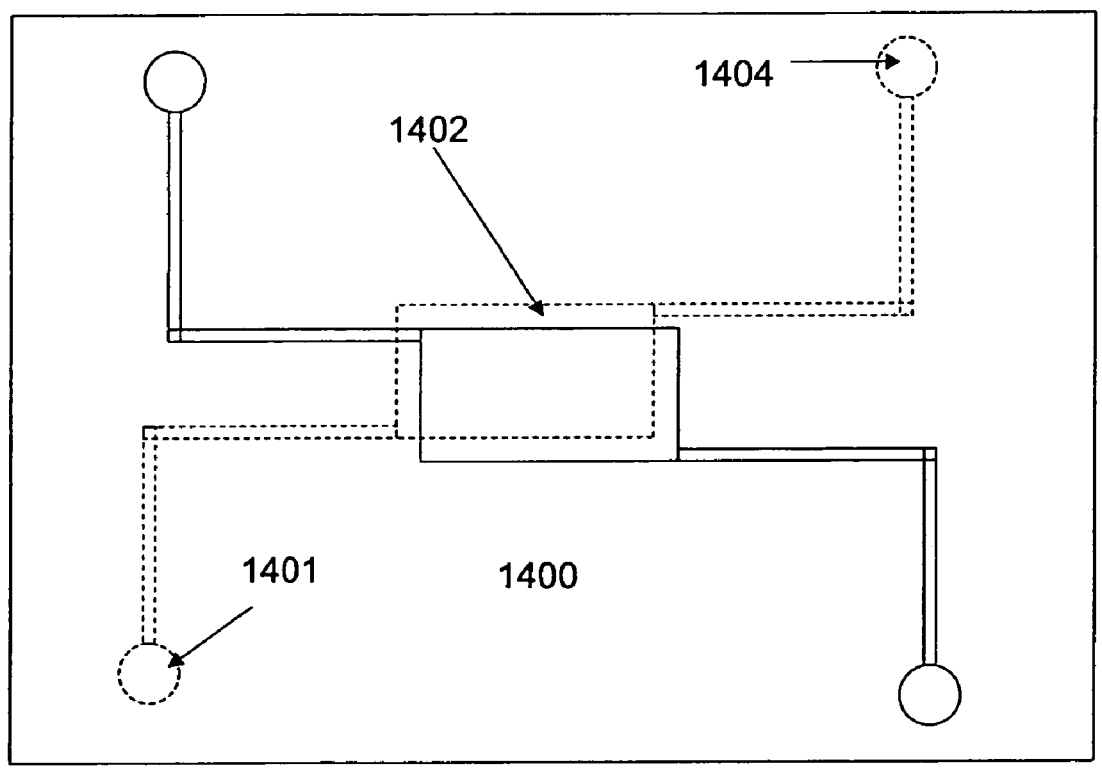
FIG. 14 depicts a microfluidic chip used within biological experiments.

An experimental chip 1400 used according to this example is represented in FIG. 14. The misalignment of the two sides and the fact one side is filled with fluorescent beads helps in disentangling the configuration in depth. As shown in FIG. 14, a sample was filled into an inlet 1401 by means of a peristaltic pump (not shown, from Ismatec) operated around 5 µL/min through a Tygon tubing of 0.19 or 0.25 mm inner diameter. Previous experiments had shown that the tube did not induce damage to our samples. In each experiment new tubes were used to avoid cross-contamination. In most cases, the chip 1400 was filled with fluid without bubbles; in the few cases where these were present, the actual fluid volume was corrected by means of measurements taken on images taken with a camera mounted on the microscope. Only one side of the chip 1400, in this case a first side 1402 was filled with fluid.

An important requirement of the filling procedure consisted in being confident that all fluid (sample) was removed from the inlet 1401 and an outlet 1404 of the chip 1400. This was accomplished by pipetting and subsequent inspection with fluorescent microscopy that no beads were present in the connection reservoirs. If fluid was detected, it was pipetted out of the reservoir up to the absence of fluorescent beads. The determination of the nominal volume of the chip 1400 was, by itself, very difficult. Because of the design of the chip 1400, the reservoir filled with liquid had a nominal volume of approximately 3000×1400×50 µm.

As a result of the chip 1400 design, two undesired phenomena occur: on one side, the pressure generated by the pump on the fluid can be very large (the ratio between the reactor section and the input capillary cross section is about 80×, meaning that the force applied onto the base in the reactor is 80× larger with respect to the base in the capillary). In addition, a movement of the material layer by 10 µm in depth determines a change of 20% in the nominal volume of the reservoir. It was determined that the base was moving during the filling process when the inlet pressure was applied. Because of this base movement, a large pressure was applied onto the material layer, so to have it touching the opposite side surface and determining an absolute reservoir volume of about twice the nominal one. Care was taken to treat the samples identically in the two filling operations.

When the chip 1400 was not exposed to the Virtual laser Valve (VLV), the rinsing procedure consisted of removing the sample by transporting an amount of buffer between 50 and 400 µL into the chip 1400. A buffer was inserted by applying a positive pressure to the inlet 1402 and collecting the fluids from the outlet 1404. The rinsing process was typically done by a series of these operations, separated by few minutes when the chip 1400 was completely empty of fluids. The rinsing speed was limited to about 50 micro litres per minute because of the capillaries' cross section. In the capillaries, this flow corresponds to a fluid speed of 0.3 m/s (1 km/h). The fluid speed inside the chip 2200 hardly achieved 0.4 cm/s, and this explained the long rinsing process (from 30 minutes to 1 hour) required in order to observe one order of magnitude drop in the beads content of the fluid—and similarly for the biological sample concentration.

The chip filling for the exposure was kept as similar as possible to the calibration filling, and the same criteria in the analysis of the beads content applied.

The VLV exposure was performed in some cases "downstream" of the laser direction, and in some cases "upstream".

The rinsing of the chip 1400 exposed to the VLV differed from the one previously explained since all four inlets were in fluidic communication. The outlet 1404 connection was connected to the peristaltic pump (independent channels) and fed with the buffer. The fluid speed was kept from 10 µL per minute to about 40 µL per minute.

In experiments where beads were present, 2 drops of 1 µL from each final eppendorf tube were taken and deposited onto a labelled microscope slide. The drop was allowed to gently evaporate, with the consequence that all the beads contained in the drop were collected onto the flat surface of the glass inside a small perimeter. An image of the beads was taken, and beads were blindly counted by means of Scion Software package. Both drops were systematically used in the analysis order to check possible errors in the process.

Drop Experiments Description

The analysis of the previous experimental procedure has indicated the possibility to eliminate systematic errors by a simplified experiment consisting of sample preparation, fluid handling double drop preparation, single drop valves exposure, double drop collection, bead measurement and biological processing.

The drop exposure was often performed together with the chip experiments, to validate the result through consistency analysis. For this reason, the sample preparation was identical, with the precautions of "equalizing" the expected results (similar final concentrations).

The double-drop preparation consisted of putting a 1 μL drop onto a piece of material layer of about 4×4 mm2 suspended onto a glass frame by its corners. The corners were attached to the glass by means of a minute drop of water, which generated attraction between the two surfaces. The sample drop had a circular shape and was deposited with a tip. Using this method, the drop never reached the edges of the material layer nor any other material. It was noticed that all drops made with the same buffer/sample were similar and attached to the material layer with a consistent contact angle determining its shape. However, it was found that the biological sample, its concentration and the buffer fluid introduced a large variability on the drop shape. The drop had a contact area of about 2 mm$^2$ in the case of pro-insulin in water buffer at 7 μg per μL, and a contact area of about 1 mm$^2$ for the E-coli culture medium with a concentration of about 1 E-6 E. coli per μL.

The single drop exposure consisted of choosing, randomly, one of two drops and exposing it to laser radiation. Since the drop surface was substantially proportional to the drop volume (tested with drops of 1-2-3 μL and camera images) there was an overall constraint in the maximum number of valves that could be opened given by the available area.

The double drop collection consisted of removing the material layer samples with the drop from the glass frame, and putting each sample into an eppendorf tube. The material layer was rinsed inside the tube by means of an inox clamp and accurately cleaned before each exposure to avoid cross-contaminations. The final eppendorf tube contained a buffer volume between 50 and 400 μL, where the base was immersed.

The experimental procedure was tested with beads, and it was noticed that after a VLV opening, the fluid entered into the aperture and filled the VLV volume. Surface tension avoided that the fluid wets the surface opposite to the drop.

Using the above procedures, an experiment aimed to test the viability of ampicillin resistant *Escherichia Coli* (*E-Coli*) bacteria exposed to the effects of the virtual laser valve. Bacteria were provided in solution for testing purposes and returned for evaluation also in solution. Triplicate plating, at different dilutions, was performed for each of the returned samples. The original bacteria concentration was kept at about 5E5 *E-Coli*/μL in a culture buffer and the sample was mixed with beads in the same buffer at a concentration of 50 beads per μL.

The experimental chip, similar to chip 1400 as shown in FIG. 14, had a 2000×2000 um nominal reactor. The chip 1400 was filled without evidence of clogging and substantially no bubbles were evident in any of the relevant steps. The rinsing strategy consisted in 4 rinsing steps of 100 μL each, in order to observe and measure the beads/*E-coli* content in the samples.

The drop experiment was performed in quadruplicate and the material layer was removed from the eppendorf before it was sent for analysis. Two negative samples, as well as two calibration samples were present in the dataset. The calibration samples were diluted in order to generate the same colony counting of the chips experiment, in the hypothesis of 310 nL volumes (nominal) and perfect rinsing.

As shown in table 1 below the data was renormalized in both columns to the average of calibration and calibration II. The corresponding numbers are 181.5 colonies and 43.3 beads respectively, in line with expectations.

TABLE 1

|  | Colonies | Beads |
|---|---|---|
| Calibration 1 | 101.9% | 112.1% |
| Negative 1 | 0.0% | 4.6% |
| NOVLV Chip 1 | 106.3% | 87.9% |
| NOVLV Chip 2 | 41.3% | 38.2% |
| NOVLV Chip 3 | 22.0% | 30.1% |
| NOVLV Chip 4 | 16.0% | 17.3% |
| VLV Chip 1 | 87.1% | 52.0% |
| VLV Chip 2 | 29.2% | 43.9% |
| VLV Chip 3 | 13.8% | 12.7% |
| VLV Chip 4 | 15.4% | 16.2% |
| Calibration 2 | 98.1% | 87.9% |
| Negative 2 | 0.0% | 2.3% |
| VLV Drop 1 | 56.2% | 72.8% |
| NOVLV Drop 1 | 116.3% | 83.2% |
| VLV Drop 2 | 75.5% | 102.9% |
| NOVLV Drop 2 | 86.5% | 116.8% |
| VLV Drop 3 | 67.8% | 90.2% |
| NOVLV Drop 3 | 86.5% | 99.4% |
| VLV Drop 4 | 84.3% | 97.1% |
| NOVLV Drop 4 | 66.1% | 102.9% |

The colonies were plated in duplicate at different concentration and both plates were consistent. The same parameters applied to the beads.

Both the calibration and negative samples were fully compatible regarding beads and colony counting. Since beads counting resulted from the average of two drops containing approximately 50 beads, the statistical error of 10% was expected.

The NOVLV drops could be considered as an additional calibration sample. In terms of the colonies the average was 89%, while in terms of beads the average was 101%.

Figure 15:
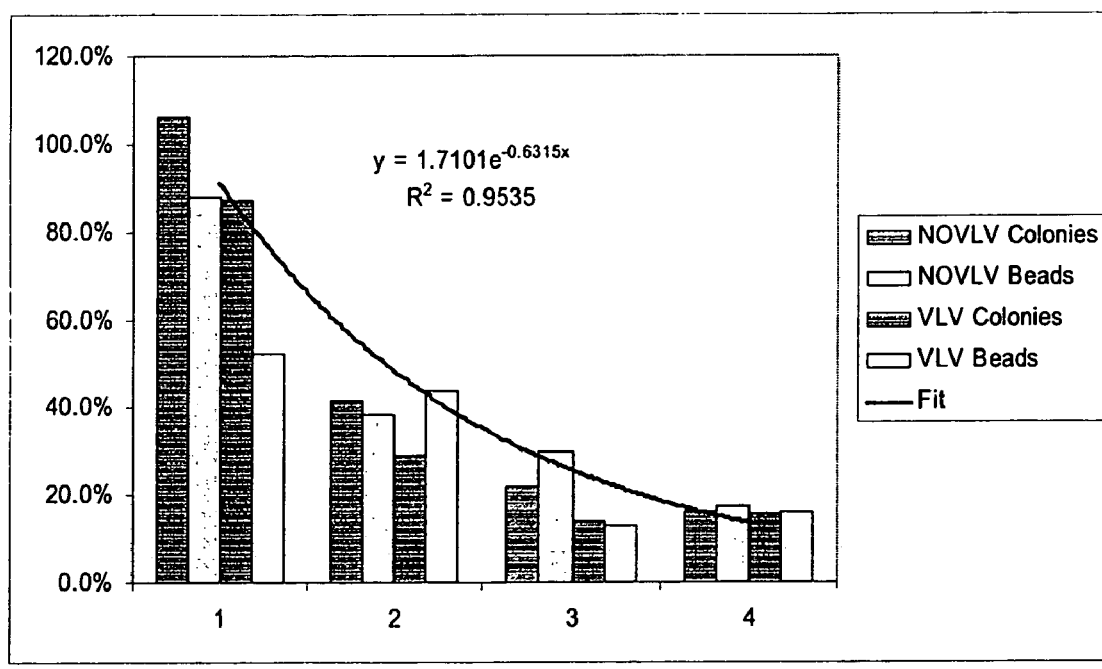
FIG. 15 is a graphic representation of chip rinsing data within the biological experiments.

The chip rinsing data is depicted in FIG. 15. The samples refer to 100 μL data points that translated into a rinsing decay constant of 157 μL. There was no striking difference between beads and colonies suggesting that the rinsing is essentially independent from the type of particle to be rinsed. Less than 7% of the samples were expected to remain in the chip and therefore since this amount was less than the experimental error there was no correction as a result.

The physical chip volume was estimated by imaging the chip and was found to be approximately 520 nL. This volume included capillaries and base bending onto the side. The volume corresponded to 167%. The integral counts from the chips are as follows:

| Integral reference Data | 185.67% |
|---|---|
| Integral Reference Beads | 173.41% |
| Integral VLV Data | 145.45% |
| Integral VLV Beads | 124.86% |

Figure 16:
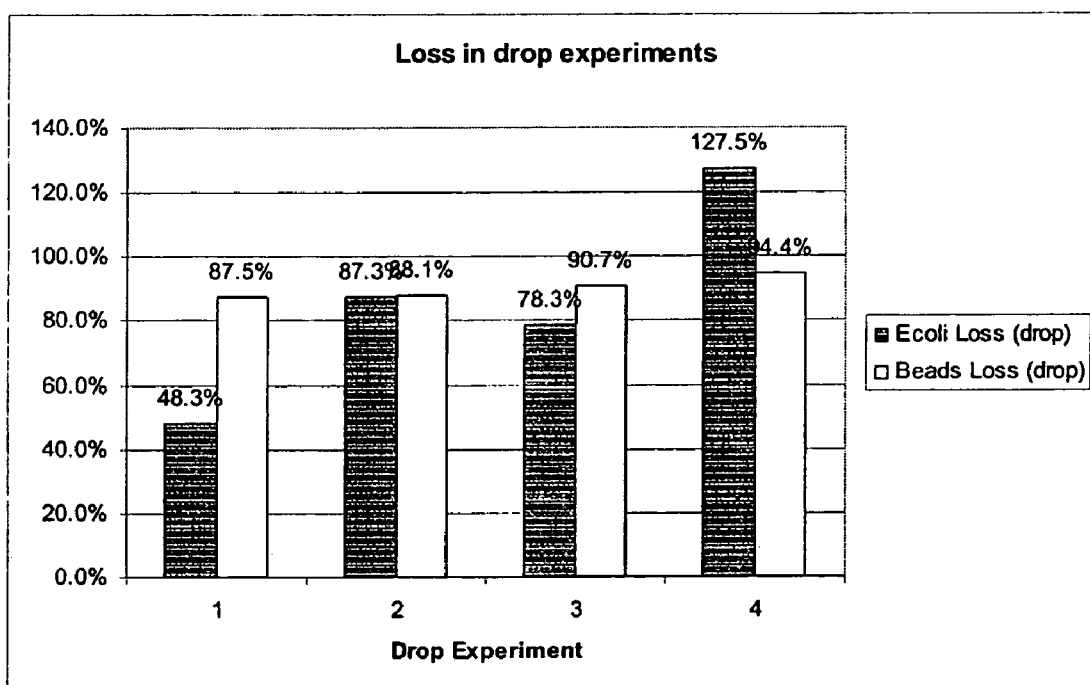
FIG. 16 is a graphic representation of the ratio between unexposed drops and exposed drops.

Well matching the expectation for the NOVLV data. The measurement of the loss comes from the VLV/NOVLV ratio and corresponded to a loss of 28% for the bead and 22% of the bacteria. The reduction of the beads and bacteria viability suggested that the *E-Coli* were damaged by the VLV similar to the beads. This result was independently verified by the drop experiments. The ratio between unexposed drops and exposed drops is graphically depicted in FIG. 16, both for *E-Coli* and beads.

Data showed a consistent loss of 10% of the beads when the drop was exposed. *E-Coli* loss was equivalent in the sense that on average 15% less *E-Coli* were present in the exposed drops with respect to the unexposed drops. It was concluded that every 10× valve appeared to reduce the sample by less than 0.7 nL inside the chip and less than 0.9 nL in the drop experiments. Therefore there was a loss of 0.83 nL per valve for *E. coli* and 0.79 nL per valve for the beads.

Example 5

The resistance of DNA plasmids coding ampicillin resistance to damage by the virtual laser valve was explored. This resistance was determined by measuring the resistance of cells to ampicillin after being transfected with the same material. Sample DNA at high concentration was provided in a TE buffer and the sample was mixed with beads at a concentration of 50 beads per microlitre. The chip used in this example was a 2000×2000 µM nominal reactor and the rinsing strategy consisted of two rinsing steps of 400 µL each. The drop experiment was performed in triplicate and the base was removed from the Eppendorf before it was sent for analysis. All samples used were diluted into a 400 µL buffer volume.

A negative sample as well as a calibration sample was included in the dataset. The calibration sample was diluted to generate the same colony counting of the chip experiment and the hypothesis of 310 nL volume (nominal) and perfect rinsing.

The following data as shown in table 2 below was renormalized to the calibration sample according to the general procedure set forth in the above examples. The corresponding counting for the calibration samples is 336 colonies of transfected cells. Transfection was performed in duplicate and in the case of "Calibration", NOVLV Chip1", "VLV Drop 1" and NOVLV Drop 2", the transfection in duplicate was repeated a second time.

TABLE 2

| | |
|---|---|
| Calibration | 100.0% |
| Negative sample | 0.3% |
| NOVLV Chip 1 | 304.5% |
| NOVLV Chip 2 | 7.7% |
| VLV Chip 1 | 188.1% |
| VLV Chip 2 | 12.8% |
| VLV Drop 1 | 83.3% |
| NO VLV Drop 1 | 81.3% |
| VLV Drop 2 | 67.6% |
| NOVLV Drop 2 | 66.4% |
| VLV Drop 3 | 44.0% |
| NOVLV Drop 3 | 51.2% |

The negative sample matched expectations. Additionally, the rinsing of the chip was performed with 400 µL volumes instead of 100 µL and the data for the second rinsing step matched the expectation from previous data.

The physical chip volume was estimated by imaging the chip to be 165% in the scale expressed in table 2 and the integral counts fro the chips were as follows:

| | |
|---|---|
| Integral Reference Data | 312.20% |
| Integral VLV data | 200.89% |

Notably, the amount of DNA extracted from the unexposed chip was about a factor twice as large as expected. The hypothesis of a change in the transfection efficiency was dismissed by the repetition of the transfection step, done in the same time for the calibration sample and for the dominant point (NOVLV Chip 1).

The face value ration between the exposed and the unexposed chip points to a 35% loss of DNA, however, the exposed sample has a counting rate of colonies compatible with expectation from the geometrical volume of the chip.

Figure 17:
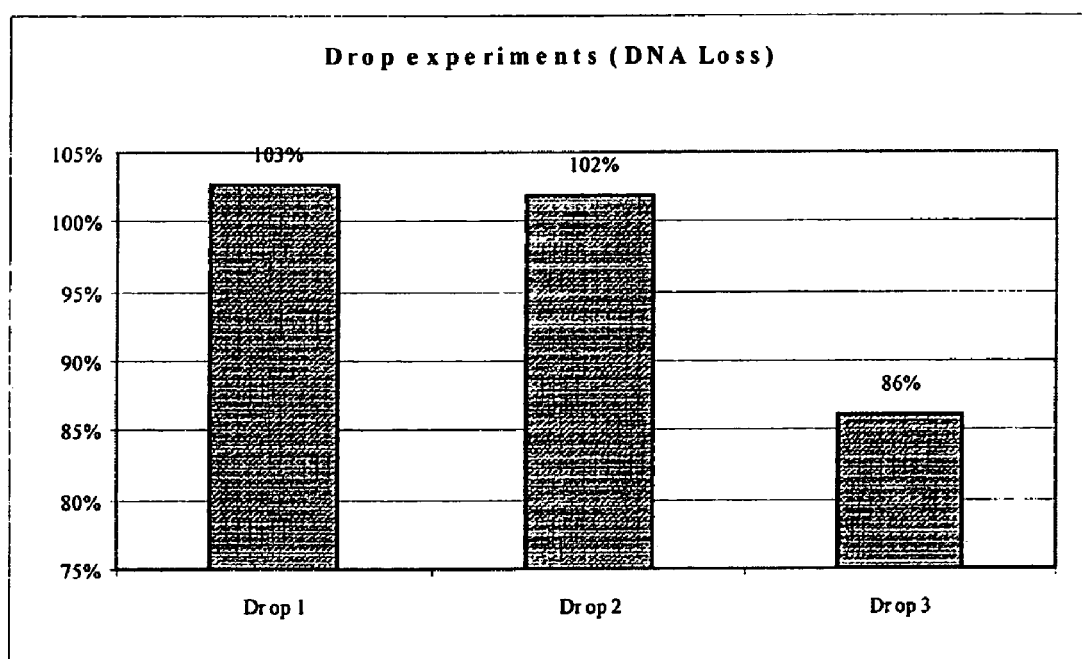
FIG. 17 is a graphic representation of the results of the drop experiments.

The results of the drop experiments are depicted in FIG. 17. The average result suggests a 3% loss.

Example 6

This experiment consisted in producing one VLV drop, one NOVLV drop and one microlitre calibration sample of human pro-insulin at 7 microgram per microlitre. The drops on the base were immersed in a 50 µL buffer. Some problems were experienced with the behavior of the protein with the tips used, since the affinity of the fluid with the material of the tip was significantly higher than expected. The drop exposure was modified in order to avoid possible contacts of the backside of the drop with parafilm. The final eppendorf tubes were sent for analysis still containing the base samples exposed. No beads were used in the process.

Approximately 1.3 µL of the sample solution was used for HPLC injection and HPLC was performed in triplicate for each eppendorf. The peaks shape was analyzed and no evidence of differences between the three samples was found. It appeared that no alteration or modification of the sample protein occurred. Further analysis was performed using quadrupole MS and confirmed the HPLC conclusion.

Example 7

Base loading optimization has been studied by varying the shot energy by means of a different laser shot pulse length, with the aim to find the perforation limit for bases of different materials, thickness and absorption properties. The setup is substantially optimized for efficient light collection and focusing precision (CCD imaging of the focusing spot by analysis of the epi-reflected light from the base). Once these limit conditions are found, an absorption measurement of the light for the various samples has been made, using the same laser light source but at a smaller intensity, and measuring the transmitted energy by means of a PEM 100 pyrometer by Lasertechnik Berlin, Germany. The data is reported in the following tables, including the minimum laser duration (in the same conditions) that was necessary to observe the film perforation. It is visible that the minimum laser perforation conditions are in qualitative agreement with the expectation based on the base absorptivity and the laser energy, the laser spot size being identical in all experiments.

The following table shows the correlation between absorption properties and perforation conditions. Different materials and different dyes, both in type and concentration, have been subject to decreasing intensity of radiation by reducing the pulse duration of laser emission in identical conditions. Once found the minimum impulse time for perforation, a transmission measurement has been performed by comparing the laser intensity (accurately reduced in order to avoid perforation of the layer or damage of the dye) with identical material once loaded with a dye and without dye loading. It is evident from the table below that both materials and dye loading affect the perforation limits in identical irradiation conditions.

TABLE 3

| Material layer | Minimum impulse time for perforation [μs] | Film Transmission (%) |
|---|---|---|
| 10 μm PMMA base loaded with 0.1% Epolin 2057 | 15 | 66% |
| 10 μm PMMA base loaded with 0.25% Epolin 2057 | 10 | 20% |
| 10 μm base PMMA loaded with 1% Epolin 2057 | 5 | 0.5% |
| 20 (m PE loaded with carbon black | 10 | 9% |

Although the inventive valving device is described with a rotating platform dependant upon centripetal forces, it will be appreciated by those skilled in the art that such a valve may be used on any microfluidic device were it is desirable to use valving components. Likewise, it will be further appreciated that the inventive valving device can be adapted to larger scale analytical devices, with an increase of the overall laser intensity for larger valves, for example by means of laser diode bars. Likewise, it will be understood by those skilled in the art that this valving technology can be applied even for smaller scale devices, in the domain of nanotechnology. In fact, it is evident that the electromagnetic emission can be reduced down to diffraction limited spots, and the valves could be a fraction of the illuminated spot. Valves in the nanometer range are possible, compatibly with the molecular structure of the material layer involved.

Although the material layer within the inventive device utilizes dyes having certain spectral qualities, it will be appreciated by those skilled in the art that other compounds or particles having desirable absorption properties may be used to capture electromagnetic radiation in order to perforate the material layer. Likewise, it will be further appreciated that films or layers having desirable absorption properties may also be used to capture electromagnetic radiation.

Although the electromagnetic radiation is used within the inventive device to perforate a material layer, it will be appreciated by those skilled in the art that such electromagnetic radiation can be used to sublime or melt crystalline structures used for valving purposes.

Although the inventive valve used within the specification and examples concern the valving of fluids, it should be appreciated by those skilled in the art that the inventive valve may be used to valve gases or gaseous fluids. Likewise, it will be further appreciated that, many applications, for example fuel cells, thrust control in aerospace application, mixture control for combustion or the like, can utilize the inventive valving technology.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of any references cited throughout this application are hereby incorporated by reference. The appropriate components, processes, and methods of those documents may be selected for the present invention and embodiments thereof.

What is claimed is:

1. An apparatus for processing fluids comprising:
a first substrate comprising a plurality of first fluidic components;
a second substrate comprising a plurality of second fluidic components corresponding to the first fluidic components;
a material layer separating the plurality of first fluidic components from the plurality of second fluidic components said material layer is formed of a polymeric material loaded with a dye; and
electromagnetic radiation generating means for generating a selected electromagnetic radiation for directing onto the layer of material at a position corresponding to a portion of the layer located between at least a pair of corresponding fluidic components from the plurality of first fluidic components and the plurality of second fluidic components said selected electromagnetic radiation causing perforation of the material layer at the position allowing fluid communication between at least a pair of fluidic components.

2. An apparatus for processing fluids comprising:
a first substrate comprising a plurality of first fluidic components;
a second substrate comprising a plurality of second fluidic components corresponding to the first fluidic components;
a material layer separating the plurality of first fluidic components from the plurality of second fluidic components;
an electromagnetic generating means for generating a selected electromagnetic radiation for directing onto the layer of material at a position corresponding to a portion of the layer located between at least a pair of corresponding fluidic components from the plurality of first fluidic components and the plurality of second fluidic components said selected electromagnetic radiation causing perforation of the material layer at the position allowing fluid communication between at least a pair of fluidic components; and
a feedback generating means for generating an optical feedback to said electromagnetic generating means whereby perforation of said material layer is confirmed.

3. The apparatus according to claim 1, wherein said selected electromagnetic radiation is selected from the group consisting of infrared, visible and ultra-violet spectrum.

4. The apparatus according to claim 1, wherein said electromagnetic radiation generating means is selected from the group consisting of a laser, compact disk drive pickup and digital versatile disk drive pickup.

5. The apparatus according to claim 1, wherein said material layer includes a thickness from about 0.5 μM to about 100 μM.

6. The apparatus according to claim 1, wherein said material layer is selected from the group consisting of polymer foils and metallic foils.

7. The apparatus according to claim 1, wherein said material layer is a foil formed from a material selected from the group consisting of polymers, copolymers, monomers, metals, waxes, polysaccharides and liquid crystal polymers.

8. The apparatus according to claim 1, wherein said dye has optical properties that are substantially matched to said selected electromagnetic radiation.

9. The apparatus according to claim 1, wherein said material layer is treated to substantially absorb said selected electromagnetic radiation, said treatment is selected from the group consisting of dye loading, chemical surface treatment, chemical loading, optical interference and optical polarization.

10. The apparatus according to claim 1, wherein said material layer is formed of multiple layers having selected absorption properties and, wherein said absorption properties are responsive to said selected radiation.

11. The apparatus according to claim 1, wherein said material layer is formed of a polymeric material selected from the group consisting of Poly(methyl methacrylate) (PMMA), Low Density Polyethylene (LDPE), Linear Low Density Polyethylene (LLDPE), High Density Polyethylene (HDPE), Polyethylene Teraphathalate (PET), Polyethylene (PE), p olycarbonate (PC), Polyethylene Terephthalate Glycol (PETG) Polystyrene (PS), Ethyl Vinyl Acetate (EVA), and polyethylene napthalate (PEN).

12. The apparatus according to claim 1, wherein said first and second substrate are in the form of a disk wherein rotation of said apparatus produces a centripetal force on a fluid contained in one or more of said first and second fluidic components, said centripetal force causing fluids to move to an outer radial position.

13. The apparatus according to claim 1, wherein the substrate materials are selected from the group consisting of polymers, monomers, co-polymers, resins, ceramic, glass, quartz and silicon.

14. The apparatus according to claim 1, wherein said first and second substrate further contain optical components selected from the group consisting of lenses, mirrors and prisms.

15. The apparatus according to claim 1, further containing at least one more additional substrate and at least one more material layer.

16. The apparatus according to claim 1, wherein said selected radiation has a desired intensity from about 1 4J to about 100 4J and exposure time from about 1 microsecond and about 100 µM.

17. The apparatus according to claim 16, wherein said desired intensity and exposure time is about 10 µJ and about 10 µs, respectively.

18. The apparatus according to claim 16, wherein said selected radiation has a pulse geometry.

19. The apparatus according to claim 18, wherein said pulse geometry and said desired exposure time does not substantially alter a sample of interest.

20. The apparatus according to claim 1, wherein at least one substrate has an optical window allowing for on board sample detection.

21. The apparatus according to claim 1, wherein at least one substrate has a removable portion allowing for off board sample detection.

22. The apparatus according to claim 21, wherein said removable portion is a MALDI foil.

23. The apparatus according to claim 1, wherein a portion of said selected electromagnetic radiation directed upon said material layer is reflected or transmitted into a means for allowing confirmation of perforation.

24. An apparatus for multiplexing fluids comprising:
a first substrate comprising a set of input capillaries;
a second substrate comprising a set of output capillaries corresponding to the set of input capillaries;
a material layer positioned between said first substrate and said second substrate forming a valving interface between each of said input capillaries, and said output capillaries corresponding thereto said material layer is formed of a polymeric material loaded with a dye; and
a means for generating electromagnetic radiation, said generating means producing a selected radiation for directing onto said material layer said selected radiation causing perforation at a said valving interface causing fluid communication between said input capillary and said output capillary.

25. The apparatus according to claim 24, further comprising a means for optical feedback wherein said generating means produces a selected radiation for directing onto said material layer and said optical feedback means signals said generating means when said perforation occurs.

26. A method for processing fluids comprising:
providing a first substrate comprising a plurality of first fluidic components;
providing a second substrate comprising a plurality of second fluidic components corresponding to the first fluidic components;
providing a material layer separating the plurality of first fluidic components from the plurality of second fluidic components said material layer contains an optical dye having absorptive properties that absorb said electromagnetic radiation causing perforation; and
directing electromagnetic radiation onto said material layer in at least one position corresponding to at least one selected position between at least a pair of corresponding fluidic components from the plurality of first fluidic components and the plurality of second fluidic components, said electromagnetic radiation causing perforation in at least one selected position thereby allowing fluid communication between at least one pair of fluidic components.

27. The method according to claim 26, wherein said electromagnetic radiation is selected from the group consisting of infrared, visible and ultra-violet spectrum.

28. The method according to claim 26, wherein said material layer includes a thickness from about 0.5 µM to about 100 µM.

29. The method according to claim 26, wherein said material layer is selected from the group consisting of polymer foils and metallic foils.

30. The method according to claim 26, wherein said material layer is a foil formed from a material selected from the group consisting of polymers, copolymers, monomers, metals, waxes, polysaccharides and liquid crystal polymers.

31. The method according to claim 26, wherein said material layer is formed of a polymeric material loaded with a dye.

32. The method according to claim 31, wherein said dye has optical properties and said optical properties are substantially matched to said selected radiation.

33. The method according to claim 26, wherein said material layer is treated to substantially absorb said selected radiation, said treatment is selected from the group consisting of dye loading, chemical surface treatment, chemical loading, optical interference and optical polarization.

34. The method according to claim 26, wherein said material layer is formed of multiple layers having selected absorption properties wherein said absorption properties are responsive to said selected radiation.

35. The method according to claim 26, wherein said material layer is formed of a polymeric material selected from the group consisting of Poly(methyl methacrylate) (PMMA), Low Density Polyethylene (LDPE), Linear Low Density Polyethylene (LLDPE), High Density Polyethylene (HDPE), Polyethylene Terephthalate (PET), Polyethylene (PE), polycarbonate (PC), Polyethylene Terephthalate Glycol (PETG), Polystyrene (PS), Ethyl Vinyl Acetate (EVA), and polyethylene napthalate (PEN).

36. The method according to claim 26 further comprising the step of:

detecting said electromagnetic radiation in an optical feedback system wherein said perforation of said material layer is signaled to said optical feedback system thereby controlling said electromagnetic radiation means to substantially stop.

37. A disk for processing fluids comprising:
a first substrate comprising a plurality of first fluidic components;
a second substrate comprising a plurality of second fluidic components corresponding to the first fluidic components; and
a material layer separating the plurality of first fluidic components from the plurality of second fluidic components said material layer having an optical dye to absorb radiation at a selected portion wherein said absorption perforates said material layer at said selected portion allowing for fluid communication between said first fluidic components and said second fluidic components.

* * * * *